United States Patent
Devary et al.

(10) Patent No.: US 9,878,015 B2
(45) Date of Patent: Jan. 30, 2018

(54) PHARMACEUTICAL COMPOSITIONS AND METHODS FOR THE TREATMENT OF METASTATIC CANCER

(71) Applicant: IMMUNE SYSTEM KEY LTD., Jerusalem (IL)

(72) Inventors: Yoram Devary, Jerusalem (IL); Uziel Sandler, Jerusalem (IL)

(73) Assignee: IMMUNE SYSTEM KEY LTD., Jerusalem (IL)

( * ) Notice: Subject to any disclaimer, the term of this patent is extended or adjusted under 35 U.S.C. 154(b) by 0 days.

(21) Appl. No.: 15/102,094

(22) PCT Filed: Dec. 4, 2014

(86) PCT No.: PCT/IL2014/051058
§ 371 (c)(1),
(2) Date: Jun. 6, 2016

(87) PCT Pub. No.: WO2015/083167
PCT Pub. Date: Jun. 11, 2015

(65) Prior Publication Data
US 2016/0303200 A1   Oct. 20, 2016

Related U.S. Application Data

(60) Provisional application No. 61/912,156, filed on Dec. 5, 2013.

(51) Int. Cl.
*A61K 38/22* (2006.01)
*A61K 38/10* (2006.01)
*A61K 38/17* (2006.01)
*A61K 45/06* (2006.01)

(52) U.S. Cl.
CPC .......... *A61K 38/22* (2013.01); *A61K 38/1709* (2013.01); *A61K 45/06* (2013.01)

(58) Field of Classification Search
None
See application file for complete search history.

(56) References Cited

FOREIGN PATENT DOCUMENTS

| WO | 2006046239 A2 | 5/2006 |
| WO | 2007091240 A2 | 8/2007 |
| WO | 2007122622 A1 | 11/2007 |
| WO | 2008075349 A1 | 6/2008 |

OTHER PUBLICATIONS

Fiorio Pla, A. et al "Emerging role of TRP channels in cell migration: from tumor vascularization to metastasis" Frontiers in Physiology 4 Article 311: 1-12 (Nov. 5, 2013).
Benoist S. et al., "Complete Response of Colorectal Liver Metastases After Chemotherapy: Does it Mean Cure?" J. Clinical Oncology 24(24): 3939-3945 (Aug. 6, 2006).
Diaz, V. M. et al. "Specific interaction of tissue-type plasminogen activator (t-PA) with annexin II on the membrane of pancreatic cancer cells activates plasminogen and promotes invasion in vitro" Gut—Pancreas 53:993-1000 (2004 ).
Kumar, S. et al., "ST2/T1 Protein Functionally Binds to Two Secreted Proteins from Balb/c 3T3 and Human Umbilical Vein Endothelial Cells but Does Not Bind Interleukin 1" The Journal of Biological Chemistry 270 (46): 27905-27913 (1995).
J Gillibert-Duplantier, J. et al. "Gene expression profiling identifies sST2 as an effector of ErbB2-driven breast carcinoma cell motility, associated with metastasis" Oncogene 31:3516-3524 (Nov. 2012).
Uziei Sandler et al. "A Novel Human Hormone-peptide NEROFE with strong anti Cancer Activity" ISSN: 1790-5125 ISBN: 978-960-47. 156-161.
Sandler Uziel et al: "NEROFE—A novel human hormone-peptide with anti-cancer activity" 8 (4) 327-339, XP009182897 (2010).

*Primary Examiner* — Elly-Gerald Stoica
(74) *Attorney, Agent, or Firm* — Browdy and Neimark, PLLC

(57) ABSTRACT

The invention provides isolated peptides, fragments and derivatives thereof and pharmaceutical compositions comprising same that are useful for the prevention or treatment of cancer metastasis.

6 Claims, 7 Drawing Sheets

PHARMACEUTICAL COMPOSITIONS AND METHODS FOR THE TREATMENT OF METASTATIC CANCER

TECHNOLOGICAL FIELD

This disclosure generally relates to metastatic cancer therapeutics.

PRIOR ART

References considered to be relevant as background to the presently disclosed subject matter are listed below:
[1] Fiorio Pla, A. and Gkika, D. 2013 Frontiers in Physiology 4 (Article 311): 1-12.
[2] Benoist, S. et al., 2006 J. Clinical Oncology 24(24): 3939-3945.
[3] WO 2006/046239.
[4] WO 2007/122622.
[5] WO 2007/091240.
[6] WO 2008/075349.
[7] Diaz, V. M. et al. 2004 GUT 53:993-1000.
[8] Kumar, S. et al., 2002 The Journal of Biological Chemistry Vol. 270 (46): 27905-27913
[9] Gillibert-Duplantier, J. et al. 2012 Oncogene 31:3516-3524.

Acknowledgement of the above references herein is not to be inferred as meaning that these are in any way relevant to the patentability of the presently disclosed subject matter.

BACKGROUND

According to the World Health Organization, 7.6 million people worldwide died from cancer in 2008. It is well known that cancer is a generic term relating to a large group of diseases that can affect any part of the body. One defining feature of cancer is the rapid creation of abnormal cells that grow beyond their usual boundaries, and which can then invade adjoining parts of the body and spread to other organs in a process referred to as metastasis.

Metastasis is the main cause of mortality in cancer and depends on two key processes: cell migration of cancer cells invading into adjacent tissues followed by intravasation into blood/lymphatic vessels and tumor vasculature, which give access to the blood-stream (1). Cancer metastasis is known as a complex, multi-step process that leads to the spread of cancer throughout the body and sometimes requires a therapeutic approach that differs from the approach that was chosen for treating the primary cancer.

For example, in colorectal carcinoma, one of the most common cancers, approximately 50% of colorectal carcinoma patients develop liver metastases at some point during the course of their disease (2). Patients who are candidates for surgical resection of their liver metastases can expect a prolonged survival or even a cure. Unfortunately, only 10% to 25% of patients are candidates for liver resection and in patients with unresectable metastases, chemotherapy is the treatment of choice.

Complete response to a treatment in cancer is usually defined as the disappearance of target lesions on imaging. However, as reported by Benoist, S. et al. (2), in more than 25% of cases, macroscopic residual disease was found during surgical exploration at the site of liver metastases that were considered to have disappeared based on imaging. In addition, in patients with no obvious disease at surgery, microscopic cancer was observed in the resected specimen from the site of initial liver metastases in 80% of patients. Finally, in patients with no more tumor observed and in whom the site of complete response was left in place, in situ recurrence was observed in 74% of cases after 1 year.

These data show that although complete response seen on imaging may be a useful criterion for evaluating the efficacy of chemotherapy, it does not mean the cure of cancer in most cases. In addition, while certain types of metastatic cancer are treated as a chronic disease, thereby prolonging the lives of the patients, many types of metastatic cancer are still considered incurable.

A peptide termed "T101" that is encoded by a cDNA unique for the human thymus was identified. This peptide was implicated, inter alia, for the treatment of cancer via its role as a stimulator of the immune system (WO 2006/046239, 3). WO 2006/046239 demonstrates that T101 is able to stimulate the immune system and to reduce tumor size, suggesting that the peptide affects the proliferation of cancer cells. Treatment of cancer by using T101 was also suggested in WO 2007/122622 (4), which demonstrates, inter alia, the effect of T101 on the development of various types of tumors. The peptide T101 was also described in WO 2007/091240 (5), relating to treatment of immunological diseases and WO 2008/075349 (6), relating to treating or preventing a disease involving a cell having T1/ST2 receptor.

GENERAL DESCRIPTION

By one of its aspects the present invention provides a pharmaceutical composition comprising an isolated peptide comprising the amino acid sequence of SEQ ID NO: 3 or any functional fragments or derivatives of the isolated peptide for use in a method of preventing or treating cancer metastasis.

By its further aspects the present invention provides a pharmaceutical composition comprising an isolated peptide comprising the amino acid sequence of SEQ ID NO: 3 or any functional fragments or derivatives of the isolated peptide for use in a method of reducing cancer cell motility, preventing or inhibiting angiogenesis in a cancer patient or decreasing the level of vascular endothelial growth factor (VEGF) in a cancer patient.

By yet another one of its aspects the present invention provides a method of preventing or treating cancer metastasis comprising administering to a cancer patient in need thereof a pharmaceutical composition comprising a therapeutically effective amount of an isolated peptide comprising the amino acid sequence of SEQ ID NO: 3 or any functional fragments or derivatives of the isolated peptide.

In further aspects the present invention provides a method of reducing cancer cell motility, preventing or inhibiting angiogenesis in a cancer patient or decreasing the level of VEGF in the serum of a cancer patient, said methods comprising administering to a cancer patient diagnosed with cancer with a metastatic potential a pharmaceutical composition comprising a therapeutically effective amount of an isolated peptide comprising the amino acid sequence of SEQ ID NO: 3 or any functional fragments or derivatives of the isolated peptide.

In some embodiments the isolated peptide as herein defined comprises the amino acid sequence of SEQ ID NO: 1 or SEQ ID NO: 2 or any functional fragments or derivatives of the isolated peptide.

In other embodiments the isolated peptide according to the invention consists of the amino acid sequence of SEQ ID NO: 3.

In further embodiments the isolated peptide as herein defined comprises a modified amino acid sequence of SEQ ID NO: 3, in which one or more amino acid residues is replaced by conservative substitution without significantly affecting the biological characteristics of the modified peptide as compared to the unmodified peptide having the amino acid sequence of SEQ ID NO: 3.

In specific embodiments the isolated peptide as herein defined comprises a modified amino acid sequence of SEQ ID NO: 3, in which one or more amino acid residues is replaced by the corresponding D-amino acid residue.

In further specific embodiments the isolated peptide according to the invention comprises the amino acid sequence of SEQ ID NO: 4.

In still further embodiments the isolated peptide as herein defined consists of the amino acid sequence of SEQ ID NO: 4.

In the above and other embodiments the present invention relates to a cancer that is a metastatic cancer.

In some embodiments the metastatic cancer is selected from the group consisting of pancreatic cancer, colon cancer, colorectal cancer, colon adenocarcinoma, rectal adenocarcinoma, breast cancer, skin cancer, lung cancer, non small cell lung carcinoma, renal cancer, multiple myeloma, thyroid cancer, prostate cancer, adenocarcinoma, head and neck cancer, gastrointestinal cancer, stomach cancer, cancer of the small intestine, spindle cell neoplasm, hepatic carcinoma, liver cancer and malignancies of the female genital tract.

In further embodiments the pharmaceutical composition for use according to the invention is adapted for administration with at least one additional anti-cancer therapy. In some embodiments the method of preventing or treating cancer metastasis according to the invention further comprises administering to said cancer patient at least one additional anti-cancer therapy.

In other embodiments the at least one additional cancer therapy as herein defined is selected from the group consisting of an anti-angiogenic agent, a cytotoxic agent, a chemotherapeutic agent, hormonal therapy, radiation therapy and immunotherapy.

In yet other embodiments the pharmaceutical composition for use and methods according to the invention are where the administration is by a route selected from the group consisting of intravenous, intraperitoneal, intramuscular, subcutaneous, transcutaneous, topical, intraarticular, subconjunctival, oral, intranasal and intraocular.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
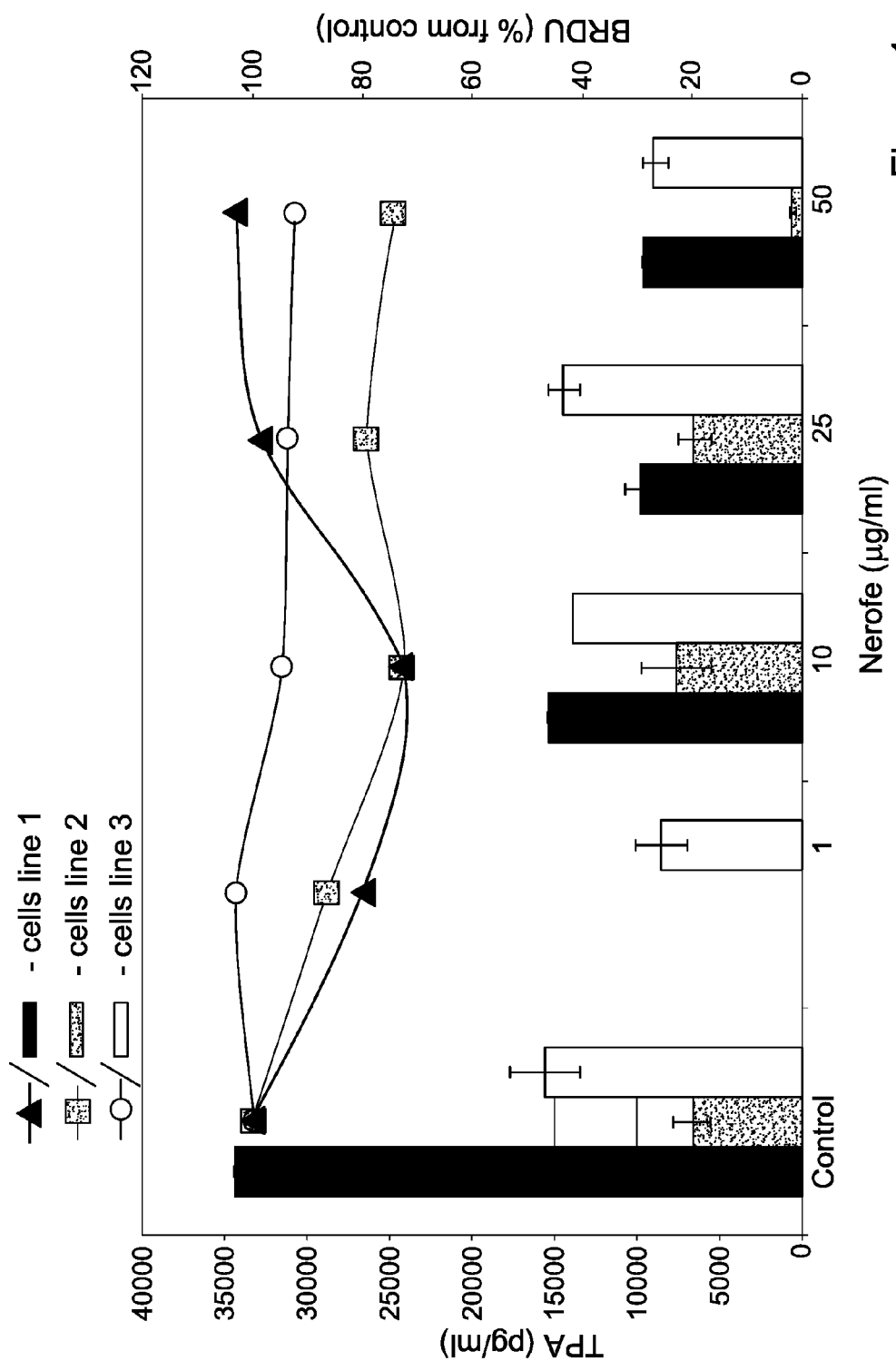
FIG. 1: a graphical presentation of the effect of the Nerofe peptide (at 1-50 μg/ml) on human adenocarcinoma pancreatic cancer cells proliferation assayed in a BrdU incorporation assay (upper lines). The lower bar graph shows the effect of the Nerofe peptide (at 1-50 μg/ml) on the ability of human adenocarcinoma pancreatic cancer cells to secrete tissue Plasminogen Activator (TPA) to the cell medium. Abbreviations: TPA, tissue plasminogen activator; BrdU, Bromodeoxyuridine; and cell line 1, cell line 2 and cell line 3, human adenocarcinoma pancreatic cancer cells.

The present invention is based on the observation that a peptide having the amino acid sequence of Trp Trp Thr Phe Phe Leu Pro Ser Thr Leu Trp Glu Arg Lys in which all of the amino acid residues are at their D configuration, termed herein "Nerofe", decreased the secretion by cancer cells of proteins that are known to be associated with cancer metastasis (i.e. tissue plasminogen activator (TPA) and soluble ST2 (sST2)). This peptide was demonstrated to directly inhibit the migration of cancer cells in vitro. In addition the peptide was shown to decrease the serum level of vascular endothelial growth factor (VEGF) in cancer patients.

Based on the decreased secretion of TPA and sST2 by cancer cells upon exposure to the Nerofe peptide, the direct effect of the peptide on the migration ability of cancer cells in vitro, and based on the effect of the Nerofe peptide on the serum levels of VEGF observed in cancer patients, the present invention provides methods and uses of the Nerofe peptide in the inhibition of cancer metastasis.

Thus in one of its aspects, the present invention provides a pharmaceutical composition comprising an isolated peptide comprising the amino acid sequence of SEQ ID NO: 3, or any functional fragments or derivatives of the isolated peptide, for use in a method of preventing or treating cancer metastasis.

The term "peptide" as herein defined refers to a molecular chain of amino acid residues, which, if required, can be modified at each one of its amino acid residues, for example by manosylation, glycosylation, amidation (for example C-terminal amides), carboxylation or phosphorylation. The peptide may be obtained synthetically, through genetic engineering methods, expression in a host cell, or through any other suitable means. Methods for producing peptides are well known in the art.

The term "isolated" refers to molecules, such as amino acid sequences or peptides that are removed from their natural environment, isolated or separated.

The peptide having the amino acid sequence of Trp Trp Thr Phe Phe Leu Pro Ser Thr Leu Trp Glu Arg Lys, in which all of the amino acid residues are L amino acid residues (denoted herein by SEQ ID NO: 3), is a C-terminal fragment of the peptide termed "full T101 peptide" that was described in WO 2006/046239 (3).

The full T101 peptide is a 84 amino acids long sequence, denoted herein by SEQ ID NO: 1. Deletion of its N-terminal 33 amino acids signal peptide yields a peptide fragment denoted herein by SEQ ID NO: 2 and termed "T101 peptide". The T101 peptide is 51 amino acids long. The amino acid sequences of SEQ ID NO: 1 and SEQ ID NO: 2, as well as of SEQ ID NO: 3 and SEQ ID NO: 4, are detailed in Table 1 below.

TABLE 1

Amino acid sequences of peptides

| SEQ ID NO. | Sequence | Description |
|---|---|---|
| 1 | MMALRSQGLMLPQSCPQLAF LTLSALAAVSFSALHLWLSG EPVQSSGTKDMRSKSDSKRV SDKQLISKAVWWTFFLPSTL WERK | Full length thymus peptide, also termed "full T101 peptide". |
| 2 | LHLWLSGEPVQSSGTKDMRS KSDSKRVSDKQLISKAVWWT FFLPSTLWERK | Full length thymus peptide, devoid of its N-terminal 33 amino acids, also termed "T101 peptide". |
| 3 | WWTFFLPSTLWERK (all L) | C-terminal 14 amino acid fragment of the "full T101 peptide" (or the "T101 peptide"). |
| 4 | WWTFFLPSTLWERK (all D) | C-terminal 14 all D amino acid fragment of the "full T101 peptide" (or the "T101 peptide"). |

The term "amino acid" as used herein, refers to naturally occurring and synthetic amino acid residues, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

The term amino acid also encompasses D-amino acids, which are mirror images of L-amino acids, where the chirality at carbon alpha has been inverted. D-amino acids are highly resistant to protease mediated degradation and have a low immunogenic response.

The terms "Amino acid sequence" or "peptide sequence" also relate to the order in which amino acid residues, connected by peptide bonds, lie in the chain in peptides and proteins. The sequence is generally reported from the N-terminal end containing free amino group to the C-terminal end containing free carboxyl group.

As exemplified below, the peptide termed herein "Nerofe", having the sequence of Trp Trp Thr Phe Phe Leu Pro Ser Thr Leu Trp Glu Arg Lys in which all of the amino acid residues are at their D configuration (denoted by SEQ ID NO: 4) was shown to decrease the secretion of TPA and sST2 by cancer cells and to directly inhibit the migration of cancer cells, suggesting its potential in inhibition of cancer metastasis.

The isolated peptide in accordance with the invention comprises at least a contiguous C-terminal fragment of the peptide termed herein "full T101 peptide", for example, but not limited to, the amino acid sequence denoted by SEQ ID NO: 3, which is the C-terminal 14 amino acid residues fragment of the full T101 peptide.

In some embodiments the isolated peptide in accordance with the invention comprises a contiguous C-terminal fragment of the full T101 peptide including at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83 or 84 amino acid residues from the C-terminus of the full T101 peptide (denoted by SEQ ID NO: 1).

Specifically, the term "isolated peptide" in accordance with the invention relates to an isolated peptide comprising the amino acid sequence denoted by SEQ ID NO: 3, or any functional fragments and derivatives of the isolated peptide. In some embodiments the isolated peptide according to the invention is the full T101 peptide as defined below (having SEQ ID NO: 1) or any functional fragments and derivatives of the isolated peptide. In other embodiments, the isolated peptide according to the invention is the thymus peptide T101 devoid of its N-terminal 33 amino acids (having SEQ ID NO: 2) or any functional fragments and derivatives of the isolated peptide.

By the term "comprising" it is meant that the isolated peptide in accordance with the invention includes the peptide denoted by SEQ ID NO: 3 or SEQ ID NO 4, but may also include additional amino acid residues at the N-terminus or at the C-terminus of the peptide denoted by SEQ ID NO: 3 or SEQ ID NO: 4, for example, but not limited to, the isolated peptide in accordance with the invention may comprise the sequences denoted by SEQ ID NO: 1 and SEQ ID NO: 2, as detailed below.

Thus in some embodiments the pharmaceutical composition for use in accordance with the invention relates to an isolated peptide comprising the amino acid sequence Trp Trp Thr Phe Phe Leu Pro Ser Thr Leu Trp Glu Arg Lys as denoted by SEQ ID NO: 3, or any functional fragments or derivatives of said isolated peptide.

In other embodiments the pharmaceutical composition for use according to the invention is wherein said isolated peptide comprises the amino acid sequence of SEQ ID NO: 1 or SEQ ID NO: 2 or any functional fragments or derivatives of the isolated peptide.

In further embodiments the pharmaceutical composition for use according to the invention is wherein said isolated peptide consists of the amino acid sequence of SEQ ID NO: 1 or SEQ ID NO: 2 or any functional fragments or derivatives of the isolated peptide.

In still further embodiments the pharmaceutical composition for use according to the invention is wherein said isolated peptide consists of the amino acid sequence of SEQ ID NO: 3.

Derivatives and modified peptides of the isolated peptides as herein defined are also encompassed by the present invention. The terms "modified", "derivatives" or "derivatives of the isolated peptide" is meant to include peptides, which differ in one or more amino acids in the overall sequence, namely, which have deletions, substitutions (e.g. replacement of at least one amino acid by another amino acid by conservative substitution), inversions or additions. This term also encompasses the replacement of at least one amino acid residue in the overall sequence by its respective D amino acid residue.

For example, the peptide Nerofe (denoted by SEQ ID NO: 4) has the amino acid sequence of SEQ ID NO: 3, in which all the amino acid residues have been replaced by their corresponding D amino acid.

Amino acid "substitutions" are the result of replacing one amino acid with another amino acid having similar structural and/or chemical properties, i.e., conservative amino acid replacements Amino acid substitutions may be made on the basis of similarity in polarity, charge, solubility, hydrophobicity, hydrophilicity, and/or the amphipathic nature of the residues involved. For example, each of the following eight groups contains amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Fragments of the peptide as herein defined are also included in the present invention. The term "fragment" refers to any peptide which is at least one amino acid shorter than the isolated peptide in accordance with the invention, obtained by deletion of at least one amino acid residue from the peptide in accordance with the invention.

Specifically, a fragment of the isolated peptide in accordance with the invention that comprises the full T101 peptide (denoted by SEQ ID NO: 1) may be a fragment of at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83 or 84 amino acid residues from the C-terminus of the full T101 peptide.

Specific modified peptides of the isolated peptide included by the present invention are isolated peptides that comprise a modified amino acid sequence of SEQ ID NO: 1, SEQ ID NO: 2, SEQ ID NO: 3 and SEQ ID NO: 4, in which one or more amino acid residues is replaced by conservative substitution without significantly affecting the biological characteristics of the modified peptide compared to the unmodified peptide having the amino acid sequence of SEQ ID NO: 1, SEQ ID NO: 2, SEQ ID NO: 3 and SEQ ID NO: 4, respectively.

In some embodiments the modified amino acid sequence of SEQ ID NO: 1, SEQ ID NO: 2, SEQ ID NO: 3 and SEQ ID NO: 4 have at least 70%, preferably 80%, more preferably 90%, in particular 100% identity to the corresponding sequences of SEQ ID NO: 1, SEQ ID NO: 2, SEQ ID NO: 3 and SEQ ID NO: 4, respectively.

The peptide derivatives in accordance with the invention also encompass any fusion protein or conjugate that comprises the amino acid sequence of SEQ ID NO: 1, SEQ ID NO: 2, SEQ ID NO: 3 or SEQ ID NO: 4 as well as any isolated peptide as herein defined that is coupled through at least one of its residues to an additional agent (for example a stabilization agent, an anti-angiogenic agent, a cytotoxic agent, etc.).

Modified fragments are also contemplated by the present invention. For example, a modified fragment may be a peptide that includes a contiguous sequence of at least 10, 15, 20, 25, 30, 35, 40, 45, 50, 55, 60, 65, 70, 75 or at least 80 amino acid residues from the C-terminus of the full T101 peptide that has a degree of identity of at least 70%, preferably at least 80%, more preferably at least 90% and particularly at least 100% to a corresponding sequence of at least 10, 15, 20, 25, 30, 35, 40, 45, 50, 55, 60, 65, 70, 75 or at least 80 included in the full T101 peptide.

It is appreciated that these peptide fragments or derivatives must not alter the biological activity of the original peptide. The terms "functional" or "without significantly affecting the biological characteristics of the modified peptide as compared to the unmodified peptide" means to denote that the modified peptide retains a biological activity qualitatively similar to that of the unmodified peptide.

The term "biological characteristics" when referring to the isolated peptide of the invention encompasses inhibition of cancer cell migration, reduction of the secreted level of tissue Type Plasminogen Activator (TPA), reduction of the secreted level of soluble ST2 in cancer cells and reduction of the secreted levels of VEGF.

In order to determine whether a peptide retains its biological characteristics qualitatively similar to that of the unmodified peptide, one or more assays can be carried out, such as for example an in vitro, in vivo or a clinical experiment in which a modified peptide is compared to the corresponding unmodified one that is assayed in parallel; or an experiment in which the modified peptide is assayed to examine whether it has a biological effect similar to that of the unmodified peptide as known from separately conducted experiment. Such an experiment may be carried out, for example, in manner described in the Examples below.

In some specific embodiments the present invention relates to functional fragments, derivatives or modified peptides, wherein said functional fragments, derivative or modified peptides have an amino acid sequence that is at least 70%, preferably at least 80%, more preferably at least 90% and particularly at least 95% identical to the amino acid sequence of the unmodified isolated peptide of the invention, namely to one of the amino acid sequences denoted by SEQ ID NO: 1, SEQ ID NO: 2, SEQ ID NO: 3 or SEQ ID NO: 4.

In other embodiments the pharmaceutical composition for use according to the invention is wherein said isolated peptide comprises a modified amino acid sequence of SEQ ID NO: 3 or SEQ ID NO: 4, in which one or more amino acid residues is replaced by conservative substitution without significantly affecting the biological characteristics of the modified peptide as compared to the unmodified peptide having the amino acid sequence of SEQ ID NO: 3 or respectively SEQ ID NO: 4.

In further embodiments the pharmaceutical composition for use according to the invention is wherein said isolated peptide comprises a modified amino acid sequence of SEQ ID NO: 3 or SEQ ID NO: 4, in which one or more amino acid residues is replaced by conservative substitution without significantly affecting the biological characteristics of the modified peptide as compared to the unmodified peptide having the amino acid sequence of SEQ ID NO: 3 or respectively SEQ ID NO: 4, wherein said modified amino acid sequence is at least 70%, preferably at least 80%, more preferably at least 90% and particularly at least 95% identical to the amino acid sequence of the unmodified peptide having the amino acid sequence of SEQ ID NO: 3 or respectively SEQ ID NO: 4.

In still further embodiments the pharmaceutical composition for use according to the invention is wherein said isolated peptide comprises a modified amino acid sequence of SEQ ID NO: 3, in which one or more amino acid residues is replaced by the corresponding D-amino acid residue.

In still further embodiments the pharmaceutical composition for use according to the invention is wherein said isolated peptide comprises the amino acid sequence of SEQ ID NO: 4.

In yet further embodiments the pharmaceutical composition for use according to the invention is wherein said isolated peptide consists of the amino acid sequence of SEQ ID NO: 4.

As exemplified below, the peptide termed herein "Nerofe" was shown to directly inhibit cell motility or migration in pancreatic cancer cells and breast cancer cells. The ability of cancer cells to migrate from their original site to a different location in the body is one of the basic steps in cancer metastasis.

The term "cancer metastasis" as herein defined refers to the process of spreading or migration of a cancer from the location where it first developed to another location or site in the body. The term cancer metastasis also relates to a tumor formed by metastatic cancer cells at a location which is different from the original site of the metastatic cancer cells. A tumor formed by metastatic cancer cells is also called a metastatic tumor.

Cancer cell metastasis usually involves the following steps: local invasion of cancer cells to nearby normal tissue; intravasation, whereby cancer cells invade and move through the walls of nearby lymph vessels or blood vessels; circulation of cancer cells through the lymphatic system and the bloodstream to other parts of the body; arrest and extravasation, whereby cancer cells arrest in small blood vessels at a distant location and then invade the walls of the capillaries and migrate into the surrounding tissue (extravasation); proliferation of cancer cells at the distant location to form small tumors known as micrometastases; and angiogenesis, the stimulation of growth of new blood vessels by micrometastases to obtain a blood supply. The most common sites of cancer metastasis are bone, liver, lung and brain.

The present invention encompasses any cancer disease that may form metastasis or secondary growth.

Predicting which types of cancer will ultimately develop metastases may be performed by a skilled physician (e.g. a physician specializing in oncology). A prediction of the metastatic potential of the cancer is based, inter alia, on the overall stage of cancer, including the size, depth, and whether or not lymph nodes are involved. Other indicators may be tumor grade and genetic and protein tests.

Identifying or diagnosing cancer metastasis may be performed by a skilled physician for example by following the appearance of symptoms such as bone pain, persistent cough, and headache which can be signs of metastatic cancer. In addition metastatic cancer may be detected by routine scans, such as blood tests, imaging (e.g. X-rays, positron emission tomography and computed tomography (PET/CT), magnetic resonance imaging (MRI), bone scan, MRI and CT) and a biopsy which is usually done to confirm a suspicious diagnosis.

Thus in some embodiments the invention relates to a cancer that is classified as a "metastatic cancer", namely any cancer type that is known in the art as having a metastatic potential.

Thus in the above and other embodiments, the cancer encompassed by the present invention is a metastatic cancer.

In specific embodiments the metastatic cancer as herein defined is selected from the group consisting of pancreatic cancer, colon cancer, colorectal cancer, colon adenocarcinoma, rectal adenocarcinoma, breast cancer, skin cancer, lung cancer, non small cell lung carcinoma, renal cancer, multiple myeloma, thyroid cancer, prostate cancer, adenocarcinoma, head and neck cancer, gastrointestinal cancer, stomach cancer, cancer of the small intestine, spindle cell neoplasm, hepatic carcinoma, liver cancer and malignancies of the female genital tract.

As shown in the appended examples, the serum level of VEGF was decreased by about 30-40% when cancer patients were administered with the peptide Nerofe, at a dose of 24 mg/m$^2$ or 48 mg/m$^2$ (given in Body Surface Area units and translates to about 0.64 or about 1.28 mg/kg body weight, respectively). The decrease in the serum level of VEGF was particularly significant for cancer patients having small intestine and rectal adenocarcinoma cancers.

As known in the art vascular endothelial growth factor (VEGF) is a signal protein produced by cells that stimulate vasculogenesis and angiogenesis. VEGF's normal function is to create new blood vessels during embryonic development, new blood vessels after injury, muscle following exercise, and new vessels to bypass blocked vessels. It is known that over-expression of VEGF may contribute to disease. Since solid cancers cannot grow beyond a limited size without an adequate blood supply, cancers that can express VEGF are able to grow and metastasize.

The observed decrease in the serum level of VEGF as a result of administering the peptide Nerofe to cancer patients is a clear anti-angiogenic effect of the Nerofe peptide.

Therefore by another one of its aspects the present invention provides a pharmaceutical composition comprising an isolated peptide as herein defined for use in a method of preventing or inhibiting angiogenesis in a cancer patient.

In one specific embodiment, the angiogenesis is tumor associated angiogenesis. In another specific embodiment the angiogenesis is associated with VEGF.

In specific embodiments the present invention provides a pharmaceutical composition comprising an isolated peptide comprising the amino acid sequence of SEQ ID NO: 3 or SEQ ID NO: 4 or any functional fragments or derivatives of the isolated peptide for use in a method of preventing or inhibiting angiogenesis.

In further specific embodiments the present invention provides a pharmaceutical composition comprising an isolated peptide consisting of the amino acid sequence of SEQ ID NO: 3 or SEQ ID NO: 4 or any functional fragments or derivatives of the isolated peptide for use in a method of preventing or inhibiting angiogenesis.

As known in the art, the term "angiogenesis" refers to the process by which new blood vessels are formed and is involved in various physiological as well as pathological processes including wound repair, reproduction, response to ischemia, arthritis, psoriasis, retinopathies, solid tumor growth and metastatic tumor spread. Angiogenesis is a highly-controlled process that is dependent on the intricate balance of both promoting and inhibiting factors.

By the terms "preventing or inhibiting angiogenesis" it is meant any restriction, retardation, reduction, decrease or diminishing of angiogenesis by at least about 1%, 5%, 10%, 15%, 20%, 25%, 30%, 35%, 40%, 45%, 50%, 55%, 60%, 65%, 70%, 75%, 80%, 85%, 90%, 95% or about 100%.

By the term preventing or inhibiting angiogenesis it is also meant the prevention or inhibition of any new blood vessel formation, including but not limited to inhibition of vasculogenesis (the de novo formation of endothelial cells from mesoderm cell precursors).

The effect of the isolated peptides as herein defined on angiogenesis may be monitored by any method known in the art, for example by imaging or by monitoring physiological markers associated with angiogenesis (for example vascular endothelial growth factor).

As known in the art and as indicated above, vascular endothelial growth factor (VEGF) is a mitogenic factor that stimulates pro-angiogenic properties, including endothelial cell migration, tube formation and proliferation. The recognition of VEGF as a primary stimulus of angiogenesis in pathological conditions has led to various attempts to block VEGF activity.

Figure 6:
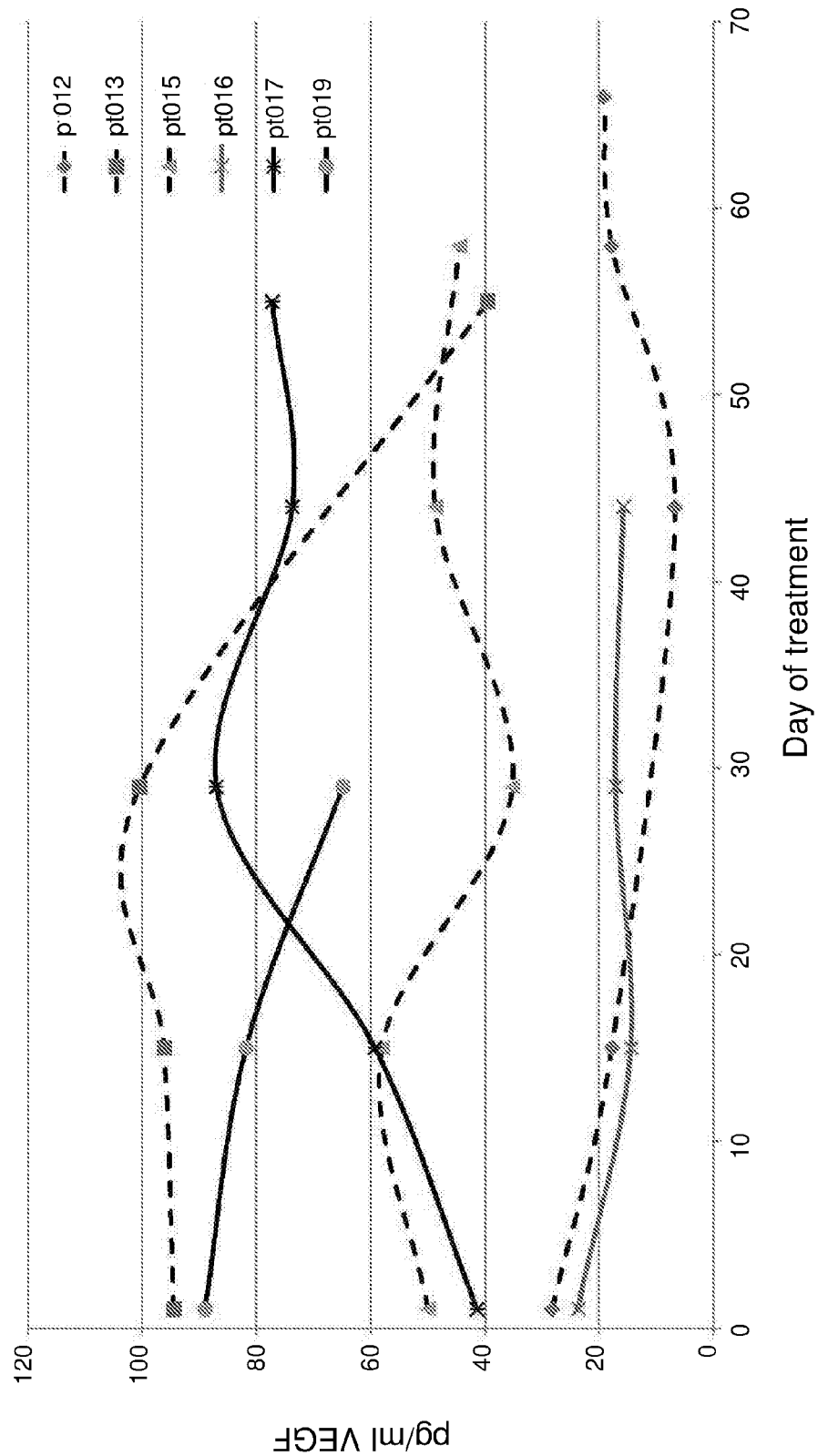
FIG. 6: graphical presentation of serum VEGF levels in patients administered with the peptide Nerofe at 24 mg/m$^2$ (0.64 mg/kg body weight, broken line) or 48 mg/m$^2$ (1.28 mg/kg body weight, full line) at the indicated time points. Abbreviations: pt012, a patient having a pancreatic cancer; pt013, a patient having a small intestine cancer; pt015, a patient having a non small cell lung carcinoma; pt016, a patient having a hepatic carcinoma; pt017, a patient having a colon adenocarcinoma cancer; and pt019, a patient having a rectal adenocarcinoma.

Without wishing to be bound by theory, the observed decrease in the serum level of VEGF as a result of administering the peptide Nerofe to cancer patients, as shown in FIG. 6, indicates an anti-angiogenic effect of the Nerofe peptide.

Therefore in yet another one of its aspects the present invention provides a pharmaceutical composition comprising an isolated peptide as herein defined for use in a method of decreasing the level of VEGF in a cancer patient.

Measuring the level of VEGF in a cancer patient administered with the isolated peptide as herein defined may be performed using any method known in the art, for example by obtaining biological samples (e.g. blood) from the patient before the beginning of the treatment with the isolated peptide as herein defined and at various time points during the treatment and thereafter. The levels of VEGF in these biological samples may be determined following procedures well known in the art.

A decrease in the level of VEGF is observed when the serum levels of VEGF in biological sample(s) obtained from a cancer patient after the beginning of the treatment with the isolated peptide as herein defined are lower than the serum levels of VEGF in biological sample(s) obtained from a cancer patient before the treatment was started.

Any decrease in the serum level of VEGF in the blood of a cancer patient administered with the isolated peptide as herein defined is encompassed by the present invention. In specific embodiments the decrease in the serum level of VEGF may be of at least about 1%, 5%, 10%, 15%, 20%, 25%, 30%, 35%, 40%, 45%, 50%, 55%, 60%, 65%, 70%, 75%, 80%, 85%, 90%, 95% or about 100%.

In specific embodiments the present invention provides a pharmaceutical composition comprising an isolated peptide comprising the amino acid sequence of SEQ ID NO: 3 or SEQ ID NO: 4 or any functional fragments or derivatives of the isolated peptide for use in a method of decreasing the level of VEGF.

In specific embodiments the present invention provides a pharmaceutical composition comprising an isolated peptide consisting of the amino acid sequence of SEQ ID NO: 3 or SEQ ID NO: 4 or any functional fragments or derivatives of the isolated peptide for use in a method of decreasing the level of VEGF.

In further embodiments the invention relates to a metastatic cancer which is associated with overexpression of VEGF. For example, the metastatic cancer as herein defined may be but is not limited to pancreatic cancer, small intestine cancer, rectal adenocarcinoma, colon cancer, colorectal cancer, spindle cell neoplasm, non small cell lung carcinoma, hepatic carcinoma and rectal adenocarcinoma.

In further specific embodiments, the invention relates to a metastatic cancer which is pancreatic cancer, breast cancer, small intestine cancer or rectal adenocarcinoma.

As known in the art, the term "pancreatic cancer" as herein defined refers to uncontrolled growth of the cells that make up the pancreas (a glandular organ located behind the stomach). These cancer cells have the ability to invade or spread to other parts of the body. There are a number of different types of pancreatic cancer, but pancreatic adenocarcinoma accounts for about 85% of cases.

The term "breast cancer" as herein defined and as known in the art refers to a cancer that forms in tissues of the breast. The most common type of breast cancer is ductal carcinoma, which begins in the lining of the milk ducts. Another type of breast cancer is lobular carcinoma, which begins in the lobules (milk glands) of the breast. Invasive breast cancer is breast cancer that has spread from where it began in the breast ducts or lobules to surrounding normal tissue.

As known in the art, the term "small intestine cancer" is a rare disease in which malignant cancer cells form in the tissues of the small intestine.

The term "rectal adenocarcinoma" relates to a disease in which cancer cells form in the tissues of the rectum. Adenocarcinomas comprise the vast majority (98%) of colon and rectal cancers and more rare rectal cancers include lymphoma (1.3%), carcinoid (0.4%), and sarcoma (0.3%).

In further specific embodiments the present invention provides a pharmaceutical composition comprising an isolated peptide comprising the amino acid sequence of SEQ ID NO: 4, or any functional fragments or derivatives of the isolated peptide, for use in a method of preventing or treating pancreatic cancer or breast cancer metastasis.

In still further specific embodiments the present invention provides a pharmaceutical composition comprising an isolated peptide consisting of the amino acid sequence of SEQ ID NO: 4, or any functional fragments or derivatives of the isolated peptide, for use in a method of preventing or treating pancreatic cancer metastasis.

The intended use of the methods and pharmaceutical compositions for use in accordance with the invention is preventing or treating cancer metastasis in a subject in need thereof.

Thus in some embodiments the methods and pharmaceutical compositions for use in accordance with the present invention are intended to prevent the formation of cancer metastases in a patient diagnosed as having cancer. In such cases, the pharmaceutical composition of the invention may be administered per se or in combination with other anti-cancer agents as a "preventive" or adjuvant plan, to be administered in addition to the main therapy that is administered to an individual diagnosed with cancer. The main therapy may be for example surgery and/or chemotherapy.

The term "Adjuvant therapy" refers to a treatment that is given in addition to the primary, main or initial treatment. Some non limiting examples of adjuvant therapy administered to a cancer patient currently known are chemotherapy, hormonal therapy, biological therapy, radiation therapy, or a combination thereof depending on the type of cancer. Adjuvant therapy is designed to lower the risk of future metastases, but is not a guarantee against recurrence.

Thus in some embodiments the pharmaceutical composition for use according to the invention is wherein said pharmaceutical composition is adapted for administration with at least one additional anti-cancer therapy.

Namely, in one of its aspects the invention provides methods and pharmaceutical composition for use in the treatment of a subject diagnosed with cancer (a cancer patient) optionally in combination with the primary, main or initial treatment, in order to prevent the development of cancer metastases.

The administration of the pharmaceutical composition according to the invention may be performed before, simultaneously with of after the administration of the at least one additional anti-cancer therapy The term "at least one additional anti-cancer therapy" as herein defined refers to any anti-cancer therapy known in the art, for example, but is not limited to, an anti-angiogenic agent, a cytotoxic agent, a chemotherapeutic agent (for example alkylating agents, anti-metabolites, topoisomerase inhibitors and cytotoxic antibiotics), hormonal therapy (for example Tamoxifen for the treatment of breast cancer), radiation therapy and immunotherapy (for example cell-based therapies, antibody therapies or cytokine therapy).

The term "anti-angiogenic agent" as herein defined refers to a substance that inhibits the growth of new blood vessels (angiogenesis). Some non-limiting examples of agents that inhibit angiogenesis are agents that reduce the production of pro-angiogenic factors and inhibitors of the VEGF pathway, to name but few. Inhibitors of the VEGF pathway may be for example tyrosine kinase inhibitors and antibodies directed against VEGF or VEGFR, such as Bevacizumab (Avastin) that binds to VEGF and inhibits it from binding to VEGF receptors.

Therefore in the above and other embodiments said at least one additional cancer therapy is selected from the group consisting of an anti-angiogenic agent, a cytotoxic agent, a chemotherapeutic agent, hormonal therapy, radiation therapy and immunotherapy.

The term "preventing" as herein defined means any restriction, retardation, reduction, decrease, hindering, inhibiting, impeding or suppressing of the formation of cancer metastases in an individual diagnosed with cancer (a cancer patient), where the cancer may optionally be diagnosed as a metastatic cancer.

The term preventing as herein defined means any restriction, retardation, reduction, decrease, hindering, inhibiting, impeding or suppressing of the formation of cancer metastases in an individual diagnosed with cancer by at least about 5%, 10%, 15%, 20%, 25%, 30%, 35%, 40%, 45%, 50%, 55%, 60%, 65%, 70%, 75%, 80%, 85%, 90%, 95%, or about 100%.

The invention also provides a pharmaceutical composition as herein defined for use in a method of treating cancer metastasis. In other words, the method in accordance with the invention may also be useful for the "treatment of cancer metastasis", which is herein defined as the prevention of continued or further spread of metastatic cancer cells after cancer metastasis was diagnosed in a cancer patient.

The term "cancer patient" or "cancer patient in need thereof" as herein defined thus refers to warm-blooded animals, in particular humans that were diagnosed as having cancer inter alia metastatic cancer. The term "treat", "treatment" or forms thereof, means to prevent, inhibit, arrest or alleviate the patient's disease or condition.

The level of hindering, inhibiting, impeding or suppressing of the formation of cancer metastases may be evaluated experimentally by performing suitable assays in the presence of the isolated peptide of the invention, as known in the art. A clinical evaluation of the level of hindering, inhibiting, impeding or suppressing of the formation of cancer metastases may be performed by a skilled physician, for example as described above.

The pharmaceutical composition or the pharmaceutical composition for use in accordance with the invention can be administered and dosed in accordance with good medical practice, for example systemically by parenteral, intravenous, intraperitoneal or intramuscular injection. In another example, the pharmaceutical composition can be introduced to a site by any suitable route including intravenous, subcutaneous, transcutaneous, topical, intramuscular, intraarticular, subconjunctival, or mucosal, e.g. oral, intranasal, or intraocular administration.

In some embodiments the administration according to the invention is by a route selected from the group consisting of intravenous, intraperitoneal, intramuscular, subcutaneous, transcutaneous, topical, intraarticular, subconjunctival, oral, intranasal and intraocular.

As exemplified below, the peptide "Nerofe" was shown to directly inhibit cell motility in pancreatic cancer cells.

Therefore in another one of its aspects the present invention provides a pharmaceutical composition comprising an isolated peptide comprising the amino acid sequence of SEQ ID NO: 3 or any functional fragments or derivatives of the isolated peptide for use in a method of reducing cancer cell motility.

In some embodiments the pharmaceutical composition as herein defined is for use in a method of reducing cancer cell motility in a cancer patient diagnosed with cancer with a metastatic potential.

By the term "reducing cancer cell motility" it is meant any partial or complete inhibition, attenuation or decrease in the ability of cancer cells to migrate from their location. Cancer cell migration may be monitored by any method known in the art, for example by the cell migration assay exemplified below.

The term "composition" or "pharmaceutical composition" as herein defined generally comprises an active agent being the isolated peptide in accordance with the invention and at least one of a buffering agent, an agent which adjusts the osmolarity thereof, and optionally, at least one pharmaceutically acceptable carriers, excipients and/or additives as known in the art.

The pharmaceutical compositions according to the invention may be prepared according to conventional techniques well known in the pharmaceutical industry. Such techniques include the step of bringing into association the active ingredients with the pharmaceutically acceptable carrier(s), excipient(s) or additive(s).

For example, the term "pharmaceutically acceptable carrier" as used herein includes any and all solvents, dispersion media, coatings, antibacterial and antifungal agents as well known in the art. Each carrier should be both pharmaceutically and physiologically acceptable in the sense of being compatible with the other ingredients and not injurious to the patient.

The pharmaceutically acceptable carrier can be a solvent or dispersion medium containing, for example, water, ethanol, polyol (for example, glycerol, propylene glycol, and liquid polyethylene glycol, and the like), suitable mixtures thereof, and vegetable oils.

Supplementary or additive active ingredients, for example additional anti-cancer agents, can also be incorporated into the pharmaceutical composition of the invention.

It should be understood that in addition to the ingredients particularly mentioned above, the formulations may also include other agents conventional in the art having regard to the type of formulation in question, for example those suitable for oral administration may include flavoring agents.

Thus in the above and other embodiments the pharmaceutical compositions and pharmaceutical compositions for use in accordance with the invention further comprises at least one pharmaceutically acceptable carrier, excipient and/or additive.

By another one of its aspects the present invention provides a method of preventing or treating cancer metastasis comprising administering to a cancer patient in need thereof a pharmaceutical composition comprising a therapeutically effective amount of an isolated peptide comprising the amino acid sequence of SEQ ID NO. 3 or any functional fragments or derivatives of the isolated peptide.

In some embodiments the method of preventing or treating cancer metastasis according to the invention is wherein said isolated peptide as herein defined comprises the amino acid sequence of SEQ ID NO: 1 or SEQ ID NO: 2 or any functional fragments or derivatives of the isolated peptide.

In other embodiments the method of preventing or treating cancer metastasis according to the invention is wherein said isolated peptide consists of the amino acid sequence of SEQ ID NO: 1 or SEQ ID NO: 2 or any functional fragments or derivatives of the isolated peptide.

In further embodiments the method of preventing or treating cancer metastasis according to the invention is wherein said isolated peptide consists of the amino acid sequence of SEQ ID NO: 3.

In still further embodiments the method of preventing or treating cancer metastasis according to the invention is wherein said isolated peptide comprises a modified amino acid sequence of SEQ ID NO: 3, or SEQ ID NO: 4, in which one or more amino acid residues is replaced by conservative substitution without significantly affecting the biological characteristics of the modified peptide as compared to the unmodified peptide having the amino acid sequence of SEQ ID NO: 3 or SEQ ID NO: 4, respectively.

In yet further embodiments the method of preventing or treating cancer metastasis according to the invention is wherein said isolated peptide comprises a modified amino acid sequence of SEQ ID NO: 3, in which one or more amino acid residues is replaced by the corresponding D-amino acid residue.

In some embodiments the method of preventing or treating cancer metastasis according to the invention is wherein said isolated peptide comprises the amino acid sequence of SEQ ID NO: 4.

In some embodiments the present invention provides a method of preventing or treating cancer metastasis comprising administering to a cancer patient in need thereof a pharmaceutical composition comprising a therapeutically effective amount of an isolated peptide consisting of the amino acid sequence of SEQ ID NO: 4.

In other embodiments the method of preventing or treating cancer metastasis according to the invention is wherein said method further comprises administering to said cancer patient at least one additional anti-cancer therapy as herein defined.

The present invention further provides a method of reducing cancer cell motility, said method comprising administering to a cancer patient diagnosed with cancer with a metastatic potential a pharmaceutical composition comprising a therapeutically effective amount of an isolated peptide comprising the amino acid sequence of SEQ ID NO. 3 or any functional fragments or derivatives of the isolated peptide.

In another one of its aspects the present invention provides a method of preventing or inhibiting angiogenesis in a cancer patient comprising administering to a cancer patient in need thereof a pharmaceutical composition comprising a therapeutically effective amount of an isolated peptide comprising the amino acid sequence of SEQ ID NO: 3 or any functional fragments or derivatives of the isolated peptide.

By still another one of its aspect the present invention provides a method of decreasing the level of VEGF in the serum of a cancer patient in need thereof comprising administering to said cancer patient a pharmaceutical composition comprising a therapeutically effective amount of an isolated peptide comprising the amino acid sequence of SEQ ID NO: 3 or any functional fragments or derivatives of the isolated peptide.

In some embodiments the method of reducing cancer cell motility, the method of preventing or inhibiting angiogenesis or the method of decreasing the level of VEGF in the serum of a cancer patient in need thereof in accordance with the present invention is wherein said pharmaceutical composition comprises a therapeutically effective amount of an isolated peptide comprising the amino acid sequence of SEQ ID NO: 4.

In other embodiments the method of reducing cancer cell motility, the method of preventing or inhibiting angiogenesis or the method of decreasing the level of VEGF in the serum of a cancer patient in need thereof in accordance with the present invention is wherein said pharmaceutical composition comprises a therapeutically effective amount of an isolated peptide consisting of the amino acid sequence of SEQ ID NO: 4.

The "therapeutically effective amount" (or amounts) of the isolated peptide in accordance with the invention for purposes herein defined is determined by such considerations as are known in the art in order to treat, prevent, inhibit, arrest or alleviate cancer metastasis.

The isolated peptide or the pharmaceutical composition comprising thereof in accordance with the invention may be administered to a patient in need thereof in a single of multiple doses at a therapeutically effective amount.

The dosing regimen and dosing schedule of administration of the isolated peptide or the pharmaceutical composition comprising same as herein defined may be determined by a skilled person based on considerations known in the art, for example but not limited to, following the clinical assay summarized in Table 3 below.

The methods of treatment and the pharmaceutical compositions for use as herein defined are intended to inhibit, hinder or slow-down the progression of cancer metastasis. Monitoring the therapeutic effect of the isolated peptide as herein defined (or the responsiveness of a cancer patient to the treatment as herein defined) may be regularly performed by a skilled physician, for example by an assessment of all tumors and following their size and metastasis or by following the symptoms of cancer metastasis in a cancer patient as known in the art, for example as described above.

For example, determining the responsiveness of a cancer patient to a treatment comprising administering a pharmaceutical composition for use as defined herein may be performed by following specific markers of cancer metastasis, for example but not limited to at least one of the level of secreted soluble ST2, TPA or VEGF from a biological sample containing cells obtained from the cancer patient before being treated by the methods and pharmaceutical compositions for use as herein defined and at a regular manner (for example once weekly, once in every two weeks, once a month) after being treated.

The term "biological sample" is used in its broadest sense. Biological samples may be obtained from animals (including humans) and encompass fluids (for example blood), solids and tissues.

In yet another one of its aspects the present invention provides use of an isolated peptide or any functional fragments or derivatives of the isolated peptide as herein defined in the preparation of a pharmaceutical composition for preventing or treating cancer metastasis.

In some embodiments the present invention provides use of an isolated peptide comprising the amino acid sequence of SEQ ID NO: 3 or SEQ ID NO: 4 or any functional fragments or derivatives of the isolated peptide in the preparation of a pharmaceutical composition for preventing or treating cancer metastasis comprising administering to a cancer patient in need thereof.

The present invention further provides the use of an isolated peptide or any functional fragments or derivatives of the isolated peptide as herein defined in the preparation of a pharmaceutical composition for reducing cancer cell motility.

In specific embodiments the invention provides the use of an isolated peptide comprising the amino acid sequence of SEQ ID NO: 3 or SEQ ID NO: 4 or any functional fragments or derivatives of the isolated peptide in the preparation of a pharmaceutical composition for reducing cancer cell motility.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols which are known in the art and not specifically described herein are generally followed as in Sambrook & Russell, 2001.

Experimental Procedures

Cell Culturing (Cell Passage)

Cells (human adenocarcinoma pancreatic cancer cells and human breast cancer cells) were grown in an incubator at 37° C., 5% $CO_2$ until reaching 70-80% density in the flask. Upon reaching 70-80% density, the cells were treated as follows: the culture medium was discarded, and the flask was washed with Trypsin EDTA (5 ml, Biological industries cat no. 03-052-1B). An additional volume of 5 ml Trypsin EDTA was then added to the cells and the cells were placed in the incubator for a few minutes (5-10 minutes) at 37° C., 5% $CO_2$ until most of the cells were detached from the flask. It is recommended to avoid tapping on the flask to increase detaching of the cells. Flasks were purchased from Nunc (cat no. 178905).

RPMI medium (10 ml) was then added to the Trypsin-treated cells. The medium was prepared by supplementing RPMI 1640 (containing L-Glutamine and 25 mM HEPES, Renium cat no. 52400) with 50 ml FBS (Biological industries cat no. 04-121-1A), 5 ml Sodium pyruvate (Biological industries cat no. 03-042-1B), 5 ml Pen-Strep (Biological industries cat no. 03-031-1B) and 5 ml Non essential amino acids (Biological industries cat no. 03-340-1B). The medium and Trypsin-treated cells were then divided into 2 flasks and each flask was supplemented with additional 15 ml fresh medium. The cells were grown 2-3 days until reaching 70-80% cell density. The above procedure was then repeated.

Preparation of the Peptide

A 14 amino acid residues long peptide, in which all of the amino acid residues are at their D configuration, having the amino acid sequence of Trp Trp Thr Phe Phe Leu Pro Ser Thr Leu Trp Glu Arg Lys (or WWTFFLPSTLWERK in a single letter code, as denoted by SEQ ID NO: 4), which is also termed herein "Nerofe" was prepared and used as follows: the peptide was synthesized by Novetide under Good Manufacturing Practice (GMP) conditions and lyophilized to powder. Nerofe powder was dissolved with Dimethyl sulfoxide (DMSO) such that 10 mg/ml or 20 mg/ml Nerofe solution was obtained and then further diluted with medium to obtain twice of the desired assay concentration, while not exceeding a concentration of total 2% DMSO in the final cell suspension. The final Nerofe concentrations used in the experiments were 1, 10, 25 and 50 µg/ml. A similar amount of DMSO was added to the control cells that were not incubated in the presence of Nerofe.

Bromodeoxyuridine (BrdU) Incorporation Assay

Human adenocarcinoma pancreatic cancer cells and human breast cancer cells were grown until reaching 70-80% density in the flask and detached from the flask using Trypsin EDTA as described above (the above protocol for cell culturing was used until the step of adding 10 ml medium to the Trypsin-treated cells). The cells suspended in medium and Trypsin were then transferred into a 50 ml conical tube and centrifuged at 300 g (10 min, 4° C.). The supernatant was then discarded and the cell pellet was re-suspended in fresh medium (2 ml medium prepared as described above).

The cells were then fluidized and additional 3 ml medium were added to the cell suspension such that the cells were re-suspended in a total volume of 5 ml medium. The cells were then counted and diluted to a concentration of 20,000 cells/ml medium. Next, the cells were placed in a 96 well plate (Nunc cat no. 167008), placing 100 µl cell suspension per well, such that each well contained 2000 cells. The cells were then incubated over-night in 37° C. in the incubator.

The concentrated Nerofe peptide was suspended in a total volume of 100 µl medium and added to the assayed cells in the 96-well plate to a final concentration of 1, 10, 25 and 50 µg/ml. Control (background) assays were performed in the absence of the peptide, namely, 100 µl medium was added to control cells.

The cells were incubated in the presence of the Nerofe peptide for 24 or 48 hours in 37° C. Then 20 µl per well of bromodeoxyuridine (BrdU) reagent (Millipore cat no. 2752, diluted 1:500 in medium) was added to the wells, 24 hours before cells were harvested. Namely, BrdU was added either immediately upon incubation with the peptide or after the first 24 hours of incubation in experiments in which the cells were incubated for 48 hours. The BrdU kit (Cell Signaling Ltd) was used according to the manufacturer's protocol.

Tissue Type Plasminogen Activator (TPA) Human ELISA Assay

Human adenocarcinoma pancreatic cancer cells were grown until reaching 70-80% density in the flask and were detached from the flask using Trypsin EDTA as described above. Cells suspended in medium and Trypsin were then centrifuged and re-suspended in 2 ml fresh medium (as described for the BrdU incorporation assay, above).

The cells were then fluidized and 3 ml medium were added to the cell suspension such that the cells were re-suspended in a total volume of 5 ml medium. Cells were counted and diluted to a concentration of 50,000 cells/ml medium. Next, the cells were placed in each well of a 6 well plate (Nunc cat no. 140675), by placing 2 ml cells culture per well such that each well contains 100,000 cells. The cells were next incubated over-night at 37° C. in the incubator.

The supernatant was discarded and replaced by 1 ml RPMI medium containing 2.5% FBS. Cells were then incubated for 24 hours or 48 hours at 37° C. in the presence of the Nerofe peptide at the final concentrations of 1, 10, 25 and 50 µg/ml. The supernatant was collected by centrifugation of the cells (5 minutes at 300 g, 4° C.) and stored at −20° C.

Next, a TPA ELISA assay was performed as follows: the supernatant was thawed and kept on ice, then diluted 1:15 with the TPA diluents provided with the kit (x1N, Abcam cat no. ab108914). The procedure was continued according to the manufacturer's protocol and ELISA plates were read at an optical density (O.D.) of 450/590.

Soluble ST2 (sST2) ELISA Assay

Human adenocarcinoma pancreatic cancer cells and human breast cancer cells (MDA-MB-231) were grown until reaching 70-80% cell density in the flask and were detached from the flask using Trypsin EDTA as described above. Cells suspended in medium and Trypsin were then centrifuged and re-suspended in 2 ml fresh medium (as described for the BrdU incorporation assay above).

The cells were then fluidized and 3 ml medium were added to the cell suspension such that the cells were re-suspended in a total volume of 5 ml medium. The cells were then counted and diluted to a concentration of 50,000 cells/ml medium. Cells at 2 ml per plate were placed in each well of a 6 well plate such that each well contained 100,000 cells. The cells were incubated over-night in 37° C. in the incubator.

The supernatant was discarded and replaced by 1 ml RPMI medium containing 2.5% FBS. The cells were then incubated for 24 or 48 hours in 37° C. in the presence of the Nerofe peptide at the final concentrations of 1, 10, 25 and 50 µg/ml. The supernatant was collected by centrifugation of the cells (5 minutes, 300 g, 4° C.) and stored at −20° C.

Next, a sST2 ELISA assay was performed as follows: first, a calibration curve was prepared for the sST2 peptide by serial dilutions of sST2 peptide (Genmed, project ID 35622 B-Form, sequence: HTVRLSRKNPSKECF) in PBS (Biological industries, 02-023-5A) from 10,000 pg/ml to 156 pg/ml. Then the supernatant samples were thawed and keep on ice (concentrated samples were diluted in PBS). Sample loading was performed by loading 100 µl duplicates of each sample and of the standard in a Maxisorp 96-wells plate (NUNC, F96 Maxisorp, 442404). The loaded plates were incubated at 4° C. overnight with gentle orbital shaking.

Samples were then washed by removing the liquid and washing the plate 3 times using a multi-pipette or an automated washer with 300 µl 0.05% TW-20 (Amresco, 0777-1L) in PBS. Samples were blocked by diluting 5% BSA (MP biomedicals, 160069) in PBS and loading 300 µl of the blocking buffer in each well. The blocking step included an incubation period of 1 hour with shaking (350 RPM) at room temperature (RT). Next, the samples were washed as described above.

Detecting of sST2 was performed by diluted anti-sST2 Affinity purified antibody (Genmed, project ID 35622 B-Form) 1:100 in diluent (0.05% TW-20, 0.1% BSA in PBS), where 100 µl of the detection antibody was loaded on each well. Samples were then incubated 1.5 hours at R.T. with shaking (350 RPM) and washed as described above. Diluted (1:500 in diluent) goat anti-rabbit HRP conjugate antibody (Cell signaling, 7074) was then loaded on each well (100 µl) and the samples were further incubated 30 minutes at R.T. with shaking. The samples were then washed as described above and developed by adding 100 µl 3,3',5, 5'-tetramethybenzidine (TMB, Milipore, ES001-500 ML) to each well, waiting for blue color development, and finally adding 100 µl 2N $H_2SO_4$ (Frutarom, 5552540). Plate absorbance was performed in a microplate reader at O.D. of 450/590 nm.

Cell Migration Assay of Human Cancer Cell

Human adenocarcinoma pancreatic cancer cells were grown until reaching 70-80% cell density in the flask and detached from the flask using Trypsin EDTA as described above. Cells suspended in medium and Trypsin were then centrifuged 10 minutes at 300 g (4° C.) and re-suspended in 2 ml fresh medium (as described for the BrdU incorporation assay above).

The cells were then fluidized and 3 ml medium were added such that the cells were suspended in a volume of 5 ml medium and subsequently counted and diluted to a concentration of 150,000 or 300,000 cells/ml medium.

Alternatively, Dulbecco's modification of Eagle's medium (DMEM, Biological Industries cat no. 01-055-1A) supplemented with 50 ml FBS (Biological industries cat no. 04-121-1A), 5 ml Hepes 1M (Biological industries cat no. 03-025-1C), 0.5 ml Amphotericin B 2500 µg/ml (Biological industries cat no. 03-029-1) and 5 ml Gentamycin sulfate 50 mg/ml (Biological industries cat no. 03-035-1) was used for cell culturing and re-suspension and the cells were re-suspended to a final concentration of 100,000 cells/ml medium.

A radius 96-well Cell Migration Assay plate (Cell Biolabs Inc. cat no. CBA-126) was prepared according to the manufacturer's protocol and each well was loaded with 100 µl cells such that each well contained 10,000, 15,000 or 30,000 cells. The cells were incubated overnight at the incubator (37° C.). Next, the supernatant was discarded and replaced by 100 µl RPMI containing 2.5% FBS. Cells were then treated by the Nerofe peptide suspended in a total volume of 100 µl medium (at the final concentrations of 1 and 10 µg/ml), such that each well contained a total volume of 200 µl. The cells were then incubated at 37° C. for 24 hours in an incubator.

Alternatively, the supernatant was discarded and replaced by 200 µl DMEM containing 2.5% 1-BS and the required treatment, namely control (without Nerofe), 10, 25 or 50 µg/ml Nerofe. The cells were then incubated at 37° C. for 48 hours in an incubator.

When the cells reached 70-80% density, the supernatant was discarded and the gel was removed from the center of the well, without affecting the attachment of cells as described in the manufacturer's protocol. Then, the area that was free of cells was photographed, using an inverted confocal microscope (at a magnification of ×40) at zero time (i.e. right after the gel was removed) and then every two hours. The assay was concluded by staining the cells according to manufacturer's protocol.

Photoshop software was used to calculate the area that was empty of cells at each time point in order to determine the pace in which the cells were advancing into that empty area. All experiments were performed in duplicates.

Example 1 Effect of the Nerofe Peptide on the Levels of Tissue Type Plasminogen Activator (TPA) in Human Pancreatic Cancer Cells It is has been reported that over-expression of tissue plasminogen activator (TPA) in pancreatic cancer cells promotes invasion and proliferation in vitro and tumor growth and angiogenesis in vivo (7).

The effect of the Nerofe peptide, having the all D amino acid sequence of Trp Trp Thr Phe Phe Leu Pro Ser Thr Leu Trp Glu Arg Lys (as denoted by SEQ ID NO: 4) on TPA secretion by pancreatic cancer cells in vitro was examined FIG. 1 (lower bar graph) shows human adenocarcinoma pancreatic cancer cells that were incubated in the presence of 1-50 µg/ml of the Nerofe peptide for 24 hours and then assessed for the levels of TPA by an ELISA assay, as described above.

As demonstrated in FIG. 1 (lower bar graph), in the presence of the Nerofe peptide, lower levels of secreted TPA were detected the tested cells (also termed herein "cell line 1", "cell line 2" and "cell line 3") as compared to the control cells which were not incubated with the peptide.

As indicated above, over-expression of TPA in pancreatic cancer cells promotes cell invasion. Consequently, a reduction in TPA levels may affect the invasion or metastatic potential of cancer cells and hence, the demonstrated reduction of TPA levels in the presence of the peptide indicates that the peptide may be effective in reducing cell motility.

Example 2 Effect of the Nerofe Peptide on the Levels of Soluble ST2 in Human Pancreatic Cancer Cells The T1/ST2 receptor (also referred to as Interleukin 1 receptor-like 1) is a member of the Toll-like receptor superfamily Both soluble and membrane-bound T1/ST2 receptors are predominantly expressed in hematopoietic tissues in vivo (8). It has been recently reported that the knockdown of the soluble form of ST2 (sST2), decreased ErbB2-induced cell motility in various cell lines (9).

Figure 2:
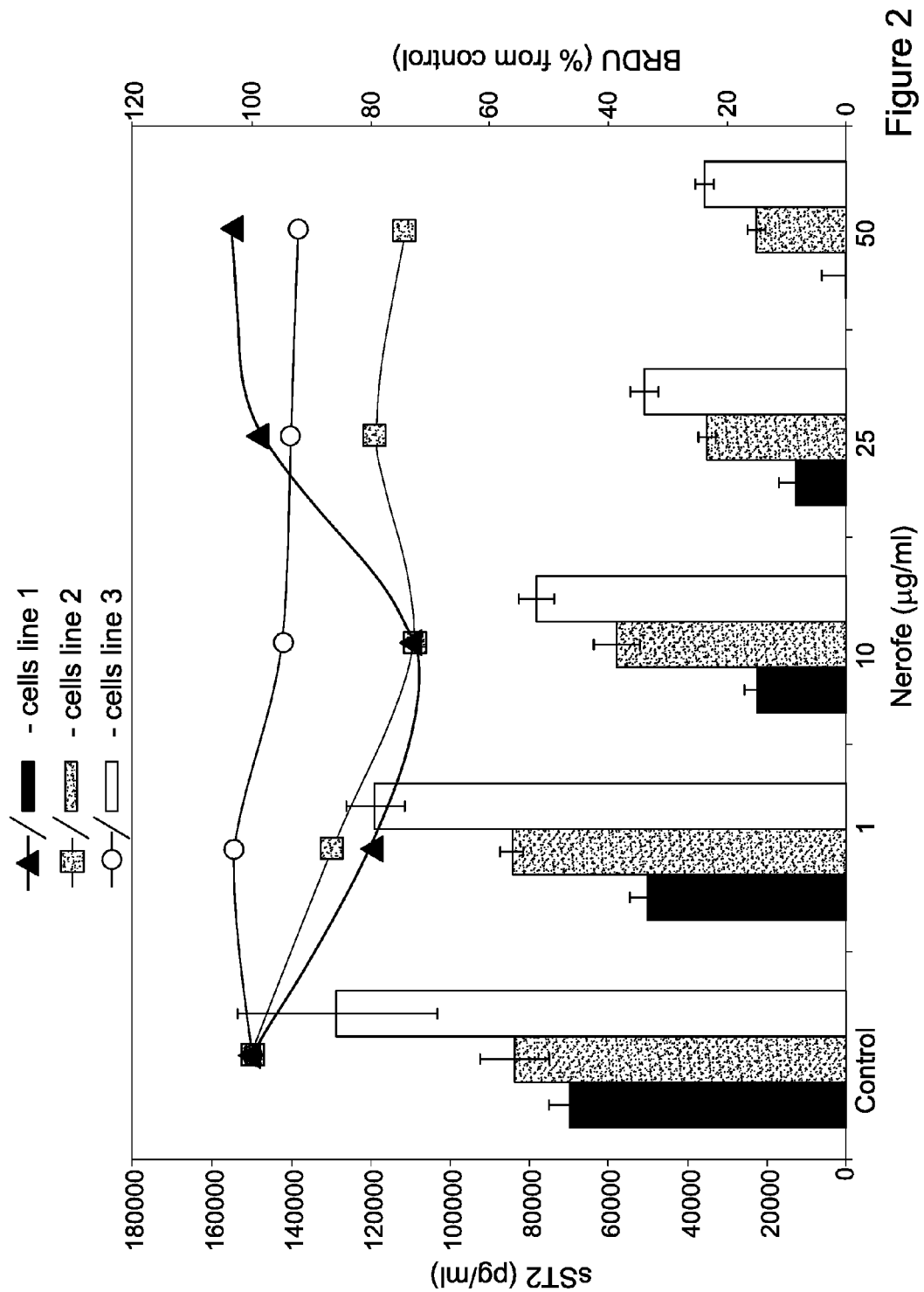
FIG. 2: are a graphical presentation of the effect of the Nerofe peptide (at 1-50 μg/ml) on human adenocarcinoma pancreatic cancer cells proliferation assayed in a BrdU incorporation assay (upper lines). The lower bar graph shows the effect of the Nerofe peptide (at 1-50 μg/ml) on human adenocarcinoma pancreatic cancer cells secretion of sST2. Abbreviations: sST2, soluble ST2; BrdU, Bromodeoxyuridine; and cell line 1, cell line 2 and cell line 3, human adenocarcinoma pancreatic cancer cells.

As demonstrated in FIG. 2 (lower bar graph), in the presence of 1-50 µg/ml of the Nerofe peptide, lower levels of sST2 were detected in all of the tested cells (human adenocarcinoma pancreatic cancer cells) as compared to the level of sST2 in cells that were not incubated with the peptide. The observed effect of the Nerofe peptide was dose-dependent. Since sST2 is associated with cell motility, the demonstrated reduction of sST2 levels in the presence of the peptide indicates that the peptide may be effective in reducing cell motility or invasion.

A decrease of about 80% in the level of sST2 was also demonstrated in human breast cancer cells (MDA-MB-231) in the presence of the Nerofe peptide under similar assay conditions (data not shown).

Example 3 Effect of the Nerofe Peptide on Human Adenocarcinoma Pancreatic Cancer Cells Proliferation A peptide consisting of the C-terminal 51 amino acid residues of the thymus peptide (termed "T101 peptide" as indicated in Table 1 above), having the amino acid sequence denoted by SEQ ID NO. 2, was previously demonstrated by the inventors to significantly reduce tumor size in adult Balb/C mice model (3).

In addition, the Nerofe peptide, which is a modified peptide fragment of the T101 peptide, consisting of the C-terminal 14 amino acid residues thereof as all D amino acid residues (denoted by SEQ ID NO. 4) was previously shown to inhibit cell proliferation in various cancer cells of hematopoietic origin. An "inhibitory effect on cell proliferation" is herein defined as at least 40% inhibition of cell proliferation in the presence of the peptide compared to a control assay conducted in the absence of the peptide.

Surprisingly, the inventors now show that the Nerofe peptide was found to have only a minor effect on human adenocarcinoma pancreatic cancer cells proliferation, as shown in the upper panels of FIG. 1 and FIG. 2.

The proliferation of human adenocarcinoma pancreatic cancer cells was assayed using a bromodeoxyuridine (BrdU) incorporation assay, for assessing the amount of cells that are synthesizing DNA, as described above. As shown in FIG. 1 and in FIG. 2 (upper lines), human pancreatic cancer cells incubated in the presence of 1, 10, 25 and 50 μg/ml of the Nerofe peptide demonstrated only a modest reduction (up to 26% inhibition) in their BrdU incorporation ability in the presence the peptide, as compared to the control assay conducted in the absence of the peptide. In addition, no correlation was found between the concentration of the Nerofe peptide and the extent of inhibition.

Example 4 Effect of the Nerofe Peptide on Cell Migration in Human Adenocarcinoma Pancreatic Cancer Cells The effect of the Nerofe peptide on cell migration was directly assayed using the Radius Cell Migration Assay, according to the manufacturer's protocol. Briefly, the cells were seeded in the well of a Radius 96-well plate (Cell Biolabs Inc. cat no. CBA-126) and adhered everywhere except in the center of the well where a biocompatible hydrogel spot was placed. Once cells formed a monolayer, the assay was initiated by gently dissolving the gel with a removal solution, leaving a gap across which cell migration can occur.

As demonstrated in Table 2 below, when the cells were incubated in the presence of the Nerofe peptide for 8 hours (at a final concentration of 10 μg/ml), migration of the cells to the center of the well was reduced by 30% for cell line 1 and by 82% for cell line 2 as compared to the control cells (which were not incubated with the peptide). Cell line "1" and cell line "2" are both adenocarcinoma pancreatic cancer cells.

These results are a direct evidence for the effect of the Nerofe peptide on the migratory potential of cancer cells.

TABLE 2

The effect of the Nerofe peptide on cell migration

| Cell line | Treatment with Nerofe (10 μg/ml) | % Migration after 8 hours | % inhibition of migration |
|---|---|---|---|
| 1 | − | 100 | |
| 1 | + | 70 | 30 |
| 2 | − | 100 | |
| 2 | + | 18 | 82 |

The effect of the Nerofe peptide on the migratory ability of human adenocarcinoma pancreatic cancer cells was further assayed under different assay conditions, namely by subjecting the cells to an incubation period of 48 hours prior to initiating the assay, in the presence of 0, 10, 25 and 50 μg/ml Nerofe peptide.

The results of an assay conducted by incubating human adenocarcinoma pancreatic cancer cells in the presence of 25 μg/ml Nerofe peptide are presented in FIG. 3. As evident from comparing FIG. 3C, obtained 27 hours after the migration assay was initiated, to FIG. 3A, obtained 1 hour after the migration assay was initiated, control cancer cells that were not treated by the Nerofe peptide migrated to the center of the plate.

Figure 3B:
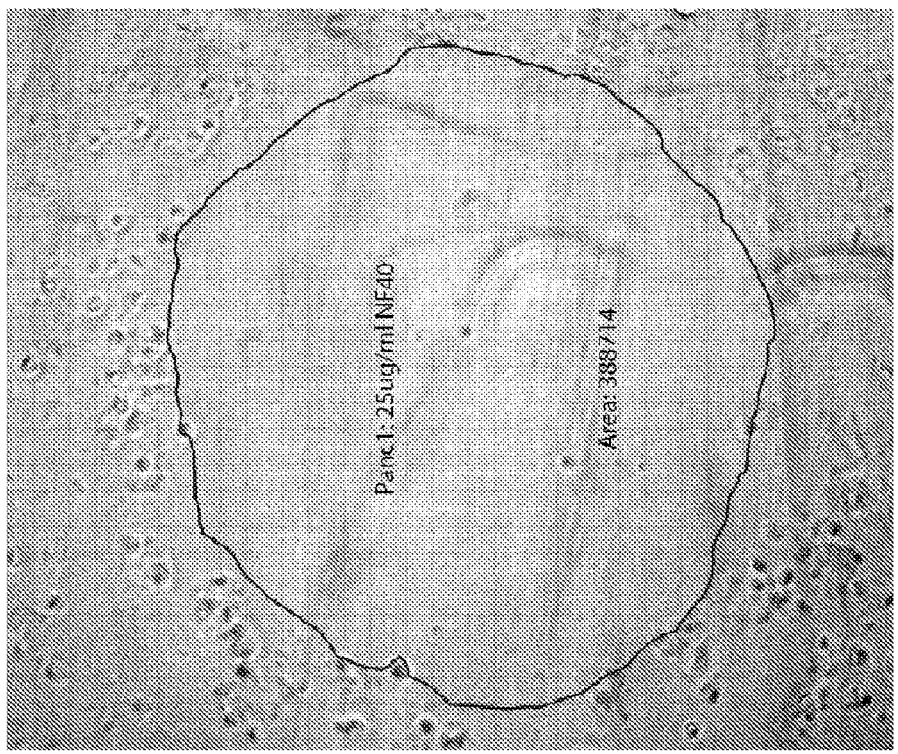
FIG. 3A-FIG. 3D: are micrographs of human adenocarcinoma pancreatic cancer cells taken at the beginning of a cell migration assay (FIG. 3A and FIG. 3B) and 27 hours after the migration assay was initiated (FIG. 3C and FIG. 3D). The cells were incubated for 48 hours prior to initiating the assay in the presence of 25 μg/ml of the Nerofe peptide (FIG. 3B and FIG. 3D) or without the peptide (FIG. 3A and FIG. 3C).
Figure 3A:
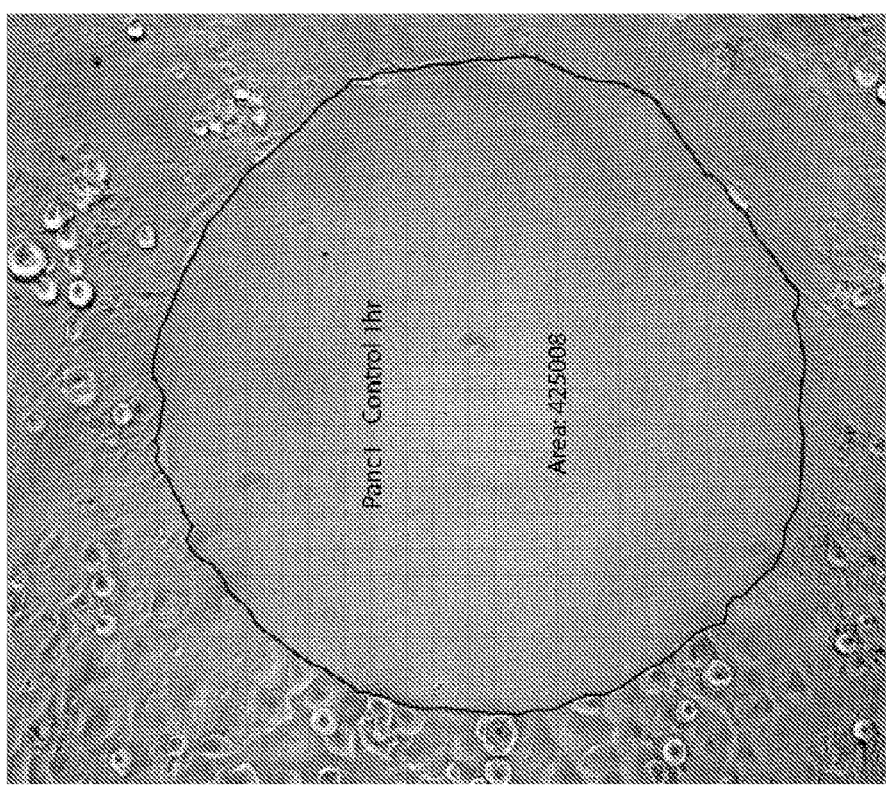
Figure 3D:
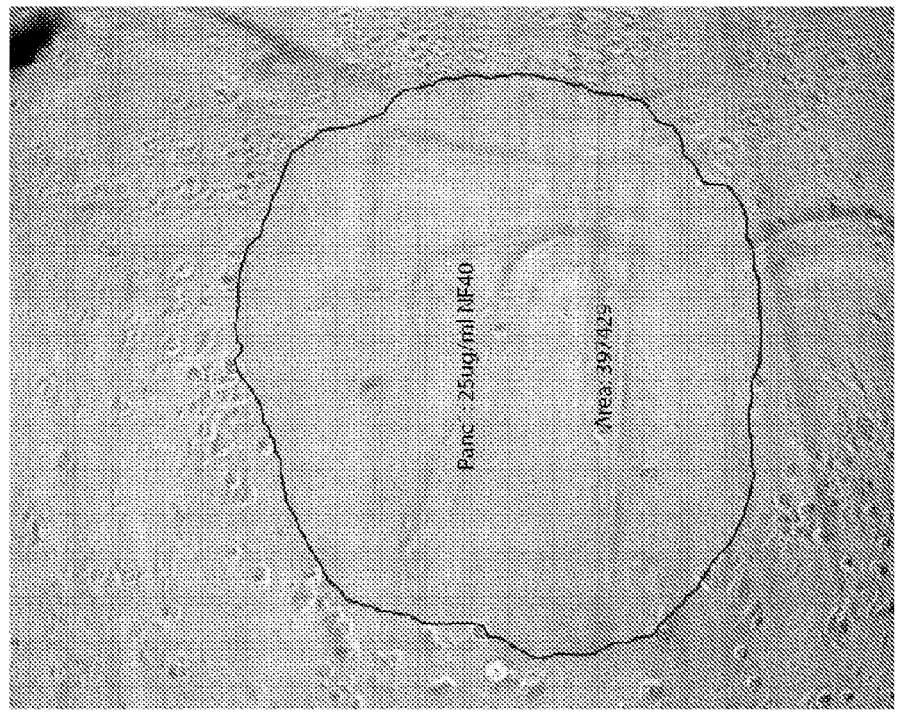
Figure 3C:
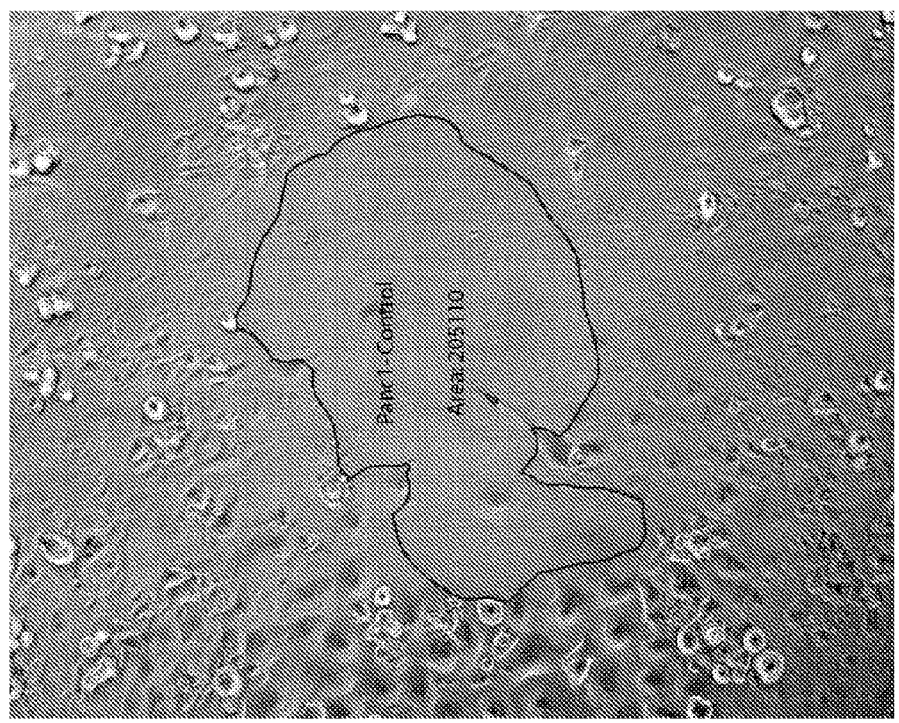

In contrast, as demonstrated by comparing FIG. 3D to FIG. 3B, migration of cells that were incubated in the presence of the Nerofe peptide was substantially inhibited.

Figure 4:
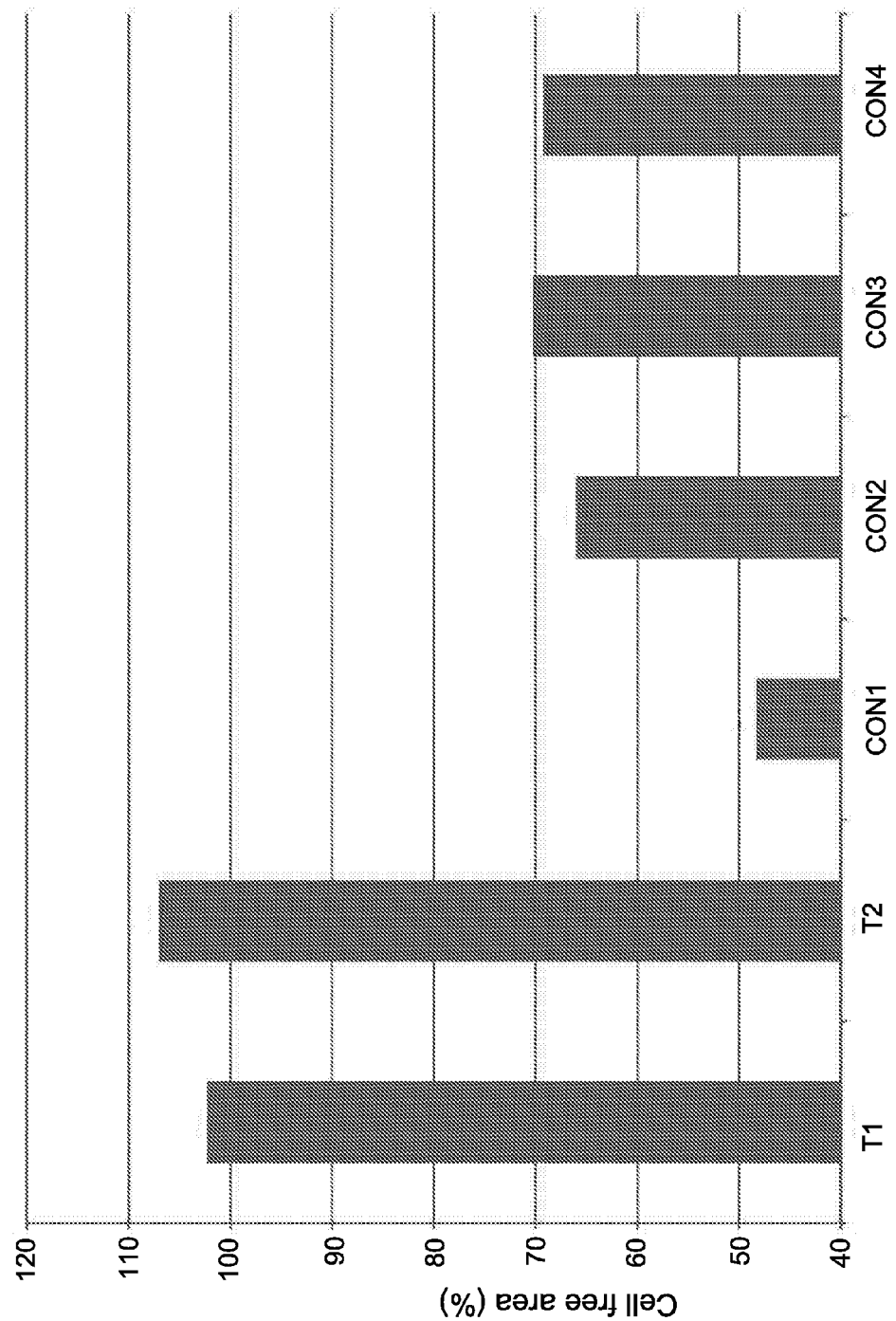
FIG. 4: is a bar graph showing the percentage of cell-free area in a cell migration assay performed using human adenocarcinoma pancreatic cancer cells that were incubated for 48 hours in the presence of 25 μg/ml of the Nerofe peptide prior to initiating the cell migration assay. Two independent assays (T1 and T2) were performed. Control cells used in four independent assays are indicated by CON1, CON1, CON3 and CON4. Percentage of cell free area was calculated by dividing the cell-free area obtained 27 hours after the experiment was initiated by the cell-free area obtained 1 hour after the experiment was initiated.

This inhibitory effect is also graphically presented in FIG. 4, which shows results obtained in two independent migration assays performed with human adenocarcinoma pancreatic cancer cells that were incubated in the presence of 25 μg/ml Nerofe peptide (T1 and T2) for 48 hours prior to initiating the migration assay and results obtained in four independent assays performed with control cells (CON1, CON2, CON3 and CON4).

As graphically shown in FIG. 4, the cell-free area in a cell migration assay conducted with cells that were previously exposed to the Nerofe peptide is substantially maintained during the migration assay, suggesting that migration of these cells is largely inhibited.

The observed reduction in the level of secreted TPA and sST2 in the presence of the Nerofe peptide, along with the direct inhibitory effect of Nerofe on cancer cell migration suggest a specific therapeutic potential for this peptide in the inhibition of cancer metastasis.

Without wishing to be bound by theory, these observed effects of the Nerofe peptide are not necessarily associated with the cellular proliferation machinery, as Nerofe was shown to have only a minor inhibitory effect on cell proliferation, as exemplified in FIG. 1 and FIG. 2.

Example 5 Effect of the Nerofe Peptide on the Serum Level of Vascular Endothelial Growth Factor in Cancer Patients Vascular endothelial growth factor (VEGF) is a signal protein produced by cells that stimulate vasculogenesis and angiogenesis. As indicated above, cancers that can express VEGF are able to grow and metastasize.

Therefore a clinical study that follows the serum levels of VEGF was conducted in cancer patients that were administered with the peptide Nerofe. Patients participating in the study were diagnosed with various cancer types, namely colon, colorectal, spindle cell neoplasm, pancreas, small intestine, non small cell lung carcinoma, hepatic carcinoma, colon adenocarcinoma and rectal adenocarcinoma, as summarized in Table 3 below.

Patients were included in at least one of Cohort 1, Cohort 2, Cohort 3 and Cohort 4 and received doses of 6, 12, 24 or 24 mg/m$^2$ (about 0.16, 0.32, 0.64 or 1.28 mg/kg body weight) of the peptide Nerofe, respectively, at the indicated time points.

Figure 5:
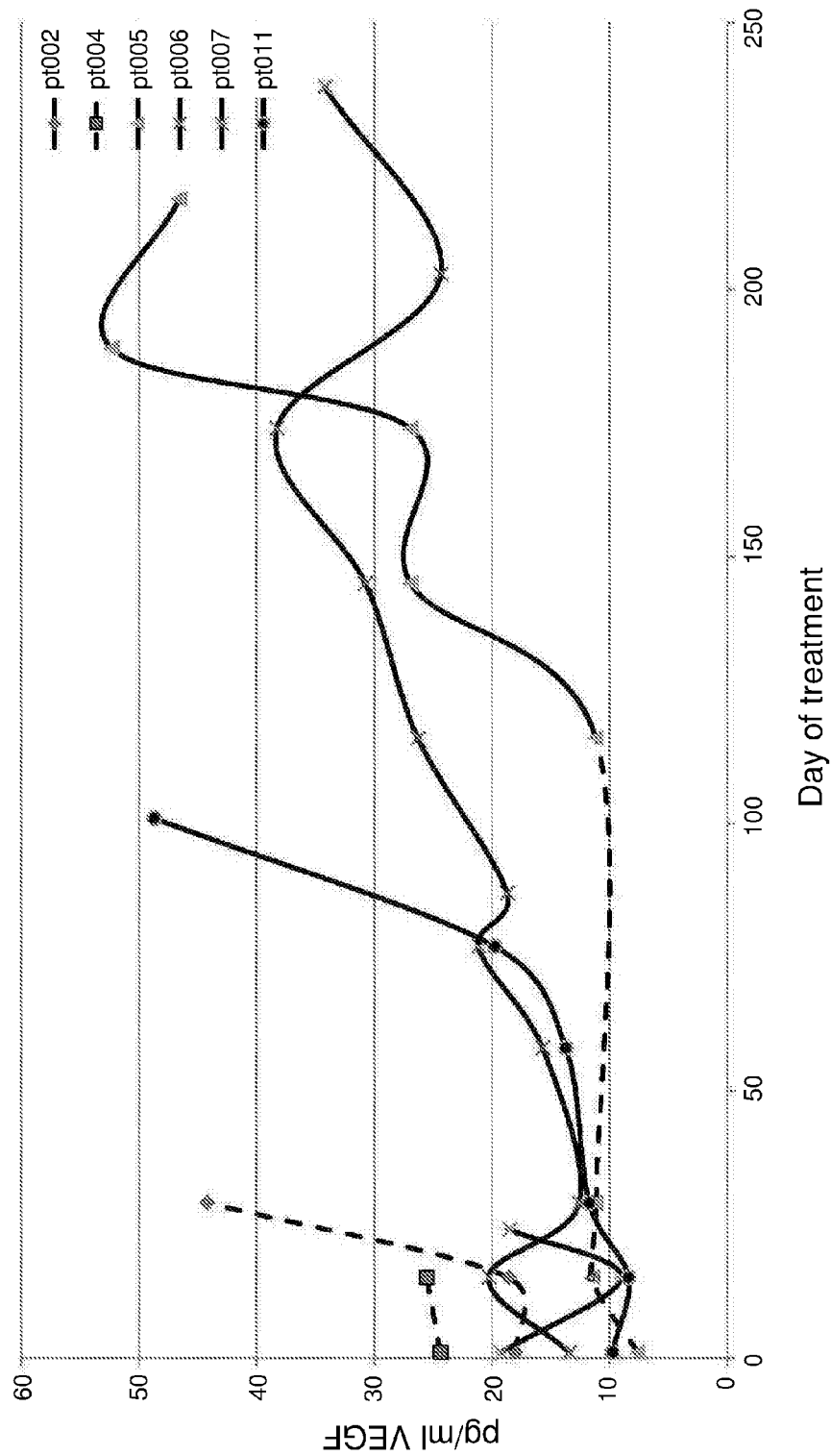
FIG. 5: graphical presentation of serum VEGF levels in patients administered with the peptide Nerofe at 6 mg/m$^2$ (0.16 mg/kg body weight, broken line) or 12 mg/m$^2$ (0.32 mg/kg body weight, full line) at the indicated time points. Abbreviations: pt002, pt004, pt007, pt011, patients having colon cancers; pt005, a patient having a colorectal cancer; and pt006, a patient having a Spindle cell neoplasm cancer.

Serum levels of VEGF were measured in blood samples obtained form these patients using an Elisa kit for human VEFG (R&D systems) and the results are presented in FIG. 5 (for the patients of Cohort 1 and Cohort 2) and in FIG. 6 (for the patients of Cohort 3 and Cohort 4).

As demonstrated in FIG. 5, in Cohort 1 and Cohort 2 there was an increase in the serum level of VEGF for the participating cancer patients. However, as demonstrated in FIG. 6, the serum levels of VEGF decreased by 30-40% in the serum of patients of Cohort 3 and Cohort 4, demonstrating a clear anti angiogenic effect for Nerofe in cancer patients.

This observed effect was particularly significant for cancer patients having small intestine and rectal adenocarcinoma cancers, namely patients 13 and 19, respectively.

TABLE 3

Summary of a clinical study with Neorfe

| Patient | Day | Cohort | Nerofe dose | Cancer type |
|---|---|---|---|---|
| 002 | 1, 15, 29 | 1 | 6 mg/m$^2$ | Colon |
| 004 | 1, 15 | 1 | 6 mg/m$^2$ | Colon |
| 005 | 1, 15, 29, 116 145, 174, 189, 217 | 1 | 6 mg/m$^2$ 12 mg/m$^2$ | Colorectal |
| 006 | 1, 15, 29, 58, 77, 87, 116 145, 174, 203, 238 | 2 3 | 12 mg/m$^2$ 24 mg/m$^2$ | Spindle cell neoplasm |
| 007 | 1, 15, 24 | 2 | 12 mg/m$^2$ | Colon |
| 011 | 1, 15, 29, 58, 77, 101 | 2 | 12 mg/m$^2$ | Colon |
| 012 | 1, 15, 44, 58, 66 | 3 | 24 mg/m$^2$ | Pancreas |
| 013 | 1, 15, 29, 55 | 3 | 24 mg/m$^2$ | Small intestine |
| 015 | 1, 15, 29, 44, 58 | 3 | 24 mg/m$^2$ | Non small cell lung carcinoma |
| 016 | 1, 15, 29, 44 | 4 | 48 mg/m$^2$ | Hepatic carcinoma |
| 017 | 1, 15, 29, 44, 55 | 4 | 48 mg/m$^2$ | Colon adenocarcinoma |
| 019 | 1, 15, 29 | 4 | 48 mg/m$^2$ | Rectal adenocarcinoma |

As metastasis and tumor cells migratation occur through blood vessels, upon decreasing the levels of VEGF, blood vessels are less permeable and metastasis may be inhibited.

The invention claimed is:

1. A method of treating, reducing or inhibiting cancer metastasis, comprising administering to a cancer patient in need thereof a pharmaceutical composition comprising a therapeutically effective amount of an isolated peptide consisting of the amino acid sequence of SEQ ID NO:4.

2. The method according to claim 1, wherein said cancer is a metastatic cancer.

3. The method according to claim 2, wherein said metastatic cancer is selected from the group consisting of pancreatic cancer, colon cancer, colorectal cancer, colon adenocarcinoma, rectal adenocarcinoma, breast cancer, skin cancer, lung cancer, non small cell lung carcinoma, renal cancer, multiple myeloma, thyroid cancer, prostate cancer, adenocarcinoma, head and neck cancer, gastrointestinal cancer, stomach cancer, cancer of the small intestine, spindle cell neoplasm, hepatic carcinoma, liver cancer and malignancies of the female genital tract.

4. The method according to claim 1, wherein said method further comprises administering to said cancer patient at least one additional anti-cancer therapy.

5. The method according to claim 4, wherein said at least one additional anti-cancer therapy is selected from the group consisting of an anti-angiogenic agent, a cytotoxic agent, a chemotherapeutic agent, hormonal therapy, radiation therapy and immunotherapy.

6. The method according to claim 1, wherein said administration is by a route selected from the group consisting of intravenous, intraperitoneal, intramuscular, subcutaneous, transcutaneous, topical, intraarticular, subconjunctival, oral, intranasal and intraocular.

\* \* \* \* \*

```
                        SEQUENCE LISTING

<160> NUMBER OF SEQ ID NOS: 4

<210> SEQ ID NO 1
<211> LENGTH: 84
<212> TYPE: PRT
<213> ORGANISM: Homo sapiens

<400> SEQUENCE: 1

Met Met Ala Leu Arg Ser Gln Gly Leu Met Leu Pro Gln Ser Cys Pro
1               5                   10                  15

Gln Leu Ala Phe Leu Thr Leu Ser Ala Leu Ala Ala Val Ser Phe Ser
                20                  25                  30

Ala Leu His Leu Trp Leu Ser Gly Glu Pro Val Gln Ser Ser Gly Thr
            35                  40                  45

Lys Asp Met Arg Ser Lys Ser Asp Ser Lys Arg Val Ser Asp Lys Gln
        50                  55                  60

Leu Ile Ser Lys Ala Val Trp Trp Thr Phe Phe Leu Pro Ser Thr Leu
65                  70                  75                  80

Trp Glu Arg Lys

<210> SEQ ID NO 2
<211> LENGTH: 51
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: isolated synthetic peptide (fragment of T 101
      peptide)

<400> SEQUENCE: 2

Leu His Leu Trp Leu Ser Gly Glu Pro Val Gln Ser Ser Gly Thr Lys
1               5                   10                  15

Asp Met Arg Ser Lys Ser Asp Ser Lys Arg Val Ser Asp Lys Gln Leu
                20                  25                  30

Ile Ser Lys Ala Val Trp Trp Thr Phe Phe Leu Pro Ser Thr Leu Trp
            35                  40                  45

Glu Arg Lys
        50

<210> SEQ ID NO 3
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 3

Trp Trp Thr Phe Phe Leu Pro Ser Thr Leu Trp Glu Arg Lys
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic peptide "Nerofe"
<220> FEATURE:
<221> NAME/KEY: MISC_FEATURE
<222> LOCATION: (1)..(1)
<223> OTHER INFORMATION: Xaa is equal to D-Trp
<220> FEATURE:
<221> NAME/KEY: MISC_FEATURE
<222> LOCATION: (2)..(2)
<223> OTHER INFORMATION: Xaa is equal to D-Trp
<220> FEATURE:
<221> NAME/KEY: MISC_FEATURE
<222> LOCATION: (3)..(3)
<223> OTHER INFORMATION: Xaa is equal to D-Thr
<220> FEATURE:
<221> NAME/KEY: MISC_FEATURE
<222> LOCATION: (4)..(4)
<223> OTHER INFORMATION: Xaa is equal to D-Phe
<220> FEATURE:
<221> NAME/KEY: MISC_FEATURE
<222> LOCATION: (5)..(5)
<223> OTHER INFORMATION: Xaa is equal to D-Phe
<220> FEATURE:
<221> NAME/KEY: MISC_FEATURE
<222> LOCATION: (6)..(6)
<223> OTHER INFORMATION: Xaa is equal to D-Leu
<220> FEATURE:
<221> NAME/KEY: MISC_FEATURE
<222> LOCATION: (7)..(7)
<223> OTHER INFORMATION: Xaa is equal to D-Pro
<220> FEATURE:
<221> NAME/KEY: MISC_FEATURE
<222> LOCATION: (8)..(8)
<223> OTHER INFORMATION: Xaa is equal to D-Ser
<220> FEATURE:
<221> NAME/KEY: MISC_FEATURE
<222> LOCATION: (9)..(9)
<223> OTHER INFORMATION: Xaa is equal to D-Thr
<220> FEATURE:
<221> NAME/KEY: MISC_FEATURE
<222> LOCATION: (10)..(10)
<223> OTHER INFORMATION: Xaa is equal to D-Leu
<220> FEATURE:
<221> NAME/KEY: MISC_FEATURE
<222> LOCATION: (11)..(11)
<223> OTHER INFORMATION: Xaa is equal to D-Trp
<220> FEATURE:
<221> NAME/KEY: MISC_FEATURE
<222> LOCATION: (12)..(12)
<223> OTHER INFORMATION: Xaa is equal to D-Glu
<220> FEATURE:
<221> NAME/KEY: MISC_FEATURE
<222> LOCATION: (13)..(13)
<223> OTHER INFORMATION: Xaa is equal to D-Arg
<220> FEATURE:
```

```
<221> NAME/KEY: MISC_FEATURE
<222> LOCATION: (14)..(14)
<223> OTHER INFORMATION: Xaa is equal to D-Lys

<400> SEQUENCE: 4

Xaa Xaa Xaa Xaa Xaa Xaa Xaa Xaa Xaa Xaa Xaa Xaa Xaa Xaa
1               5                   10
```